US006569173B1

(12) United States Patent
Blatter et al.

(10) Patent No.: US 6,569,173 B1
(45) Date of Patent: *May 27, 2003

(54) COMPRESSION PLATE ANASTOMOSIS APPARATUS

(75) Inventors: Duane D. Blatter; Kenneth C. Goodrich, both of Salt Lake City; Mike C. Barrus, Bountiful; Bruce M. Burnett, Salt Lake City, all of UT (US)

(73) Assignee: Integrated Vascular Interventional Technologies, L.C., Salt Lake City, UT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/460,740

(22) Filed: Dec. 14, 1999

(51) Int. Cl.⁷ .............................................. A61B 17/04
(52) U.S. Cl. ......................... 606/153; 606/156; 606/184
(58) Field of Search ................................ 606/152–156, 606/184

(56) References Cited

U.S. PATENT DOCUMENTS

| | | | |
|---|---|---|---|
| 1,151,300 A | | 8/1915 | Soresi |
| 2,434,030 A | * | 1/1948 | Yeomans ..................... 606/153 |
| 3,048,177 A | | 8/1962 | Takaro |
| 3,254,651 A | | 9/1962 | Collito |
| 3,254,650 A | | 6/1966 | Collito ........................ 128/334 |
| 3,258,012 A | | 6/1966 | Nakayama et al. .......... 128/334 |
| 3,435,823 A | | 4/1969 | Edwards |
| 3,774,615 A | | 11/1973 | Lim et al. |
| 4,047,654 A | | 9/1977 | Alvarado |
| 4,214,587 A | | 7/1980 | Sakura, Jr. |
| 4,233,981 A | | 11/1980 | Schomacher |
| 4,294,255 A | | 10/1981 | Geroc |
| 4,304,236 A | | 12/1981 | Conta et al. |
| 4,318,401 A | | 3/1982 | Zimmerman |
| 4,352,358 A | | 10/1982 | Angelchik |

(List continued on next page.)

FOREIGN PATENT DOCUMENTS

| | | | |
|---|---|---|---|
| WO | WO 93/00868 | 1/1993 | ............. A61F/2/06 |
| WO | WO 99/11180 | 3/1999 | ........... A61B/17/11 |

OTHER PUBLICATIONS

Jules S. Scheltes, Msc, et al., *Assessment of Patented Coronary End–to–Side Anastomotic Devices Using Micromechanical Bonding*, Ann Thorac Surg, 2000, pp. 218–221.

Ling Zhang, et al., *Venous Microanastomosis with the Unilink System, Sleeve, and Suture Techniques: A Comparative Study in the Rat*, Journal of Reconstructive Microsurgery, vol. 13, No. 4, May 1997, pp. 257–262.

Web Page, http://198.76.172.231/cgi–bin/bio/con/annuals/atseq/63/S122/1997 figs./5081f6, The Microvascular Anastomotic System as marketed by the Medical–Surgical Division of 3M Health Care, The Society of Thoracic Surgeons, 1997.

Primary Examiner—Gary Jackson
(74) Attorney, Agent, or Firm—Stoel Rives LLP

(57) ABSTRACT

Compression plates and vascular anvils for anastomosis of structures including end-to-end and end-to-side anastomosis. Vascular anvils cooperate in the opening of the anastomosis fenestra, engagement by a compression plate and subsequent eversion of the anastomosis fenestra contour, and also in establishing the contact engagement of the anastomosed structures. Compression plates hold anastomosed structures while permitting their dilation and keeping the anastomosis leak-proof. One of the compression plates assists in the eversion of the anastomosis fenestra contour. These compression plates and vascular anvils can be used with or without catheterization in minimally invasive interventions.

42 Claims, 8 Drawing Sheets

U.S. PATENT DOCUMENTS

| | | | |
|---|---|---|---|
| 4,366,819 | A | 1/1983 | Kaster |
| 4,368,736 | A | 1/1983 | Kaster |
| 4,523,592 | A | 6/1985 | Daniel |
| 4,553,542 | A | 11/1985 | Schenck et al. |
| 4,593,693 | A | 6/1986 | Schenck |
| 4,598,712 | A | 7/1986 | Rebuffat et al. |
| 4,607,637 | A | 8/1986 | Berggren et al. |
| 4,624,255 | A | 11/1986 | Schenck et al. |
| 4,624,257 | A | 11/1986 | Berggren et al. |
| 4,657,019 | A | 4/1987 | Walsh et al. |
| 4,667,673 | A | 5/1987 | Li |
| 4,721,109 | A | 1/1988 | Healey |
| 4,803,984 | A | 2/1989 | Narayanan et al. |
| 4,848,367 | A | 7/1989 | Avant et al. |
| 4,861,336 | A | 8/1989 | Helzel |
| 4,873,977 | A | 10/1989 | Avant et al. |
| 4,907,591 | A | 3/1990 | Vasconcellos et al. |
| 4,917,087 | A | 4/1990 | Walsh et al. |
| 4,917,090 | A | 4/1990 | Berggren et al. |
| 4,917,091 | A | 4/1990 | Berggren et al. |
| 4,917,114 | A | 4/1990 | Green et al. |
| 4,930,674 | A | 6/1990 | Barak |
| 4,931,057 | A | 6/1990 | Cummings et al. |
| 5,035,702 | A | 7/1991 | Taheri |
| 5,047,039 | A | 9/1991 | Avant et al. |
| 5,211,683 | A | 5/1993 | Maginot |
| 5,234,447 | A | 8/1993 | Kaster et al. |
| 5,254,113 | A | 10/1993 | Wilk |
| 5,336,233 | A | 8/1994 | Chen |
| 5,366,462 | A | 11/1994 | Kaster et al. |
| 5,456,712 | A | 10/1995 | Maginot |
| 5,456,714 | A | 10/1995 | Owen |
| 5,478,354 | A | 12/1995 | Tovey et al. |
| 5,549,122 | A | 8/1996 | Detweilwer |
| 5,591,178 | A | 1/1997 | Green et al. |
| 5,634,936 | A | 6/1997 | Linden et al. |
| 5,662,700 | A | 9/1997 | Lazarus |
| 5,695,504 | A | 12/1997 | Gifford, III et al. |
| 5,702,412 | A | 12/1997 | Popov et al. |
| 5,707,380 | A | 1/1998 | Hinchliffe et al. |
| 5,732,872 | A | 3/1998 | Bolduc et al. |
| 5,755,778 | A | 5/1998 | Kleshinski |
| 5,817,113 | A | 10/1998 | Gifford, III et al. |
| 5,830,222 | A | 11/1998 | Makower |
| 5,833,698 | A | 11/1998 | Hinchliffe et al. |
| 5,843,088 | A | 12/1998 | Barra et al. |
| 5,860,992 | A | 1/1999 | Daniel et al. |
| 5,861,005 | A | 1/1999 | Kontos |
| 5,868,763 | A | 2/1999 | Spence et al. |
| 5,868,770 | A | 2/1999 | Rygaard |
| 5,893,369 | A | 4/1999 | LeMole |
| 5,951,576 | A | 9/1999 | Wakabayashi |
| 5,954,735 | A | 9/1999 | Rygaard |
| 5,976,178 | A | 11/1999 | Goldsteen et al. |
| 6,007,576 | A | 12/1999 | McClellan |
| 6,024,748 | A | 2/2000 | Manzo et al. |
| 6,030,392 | A | 2/2000 | Dakov |
| 6,036,700 | A | 3/2000 | Stefanchik et al. |
| 6,036,703 | A | 3/2000 | Evans et al. |
| 6,042,569 | A | 3/2000 | Finch, Jr. et al. |
| 6,066,144 | A | 5/2000 | Wolf et al. |
| 6,066,148 | A | 5/2000 | Rygaard |
| 6,068,637 | A | 5/2000 | Popov et al. |
| 6,083,234 | A | 7/2000 | Nicholas et al. |
| 6,113,612 | A | 9/2000 | Swanson et al. |
| 6,152,937 | A | 11/2000 | Peterson et al. |
| 6,171,319 | B1 | 1/2001 | Nobles et al. |
| 6,176,413 | B1 | 1/2001 | Heck et al. |
| 6,187,020 | B1 | 2/2001 | Zegdi et al. |
| 6,190,396 | B1 | 2/2001 | Whitin et al. |
| 6,190,397 | B1 | 2/2001 | Spence et al. |
| 6,193,734 | B1 | 2/2001 | Bolduc et al. |
| 6,209,773 | B1 | 4/2001 | Bolduc et al. |
| 6,241,743 | B1 | 6/2001 | Levin et al. |
| 6,248,117 | B1 | 6/2001 | Blatter |
| 6,254,617 | B1 | 7/2001 | Spence et al. |
| 6,279,809 | B1 | 8/2001 | Nicolo |
| 6,280,460 | B1 | 8/2001 | Bolduc et al. |
| 6,355,050 | B1 | 3/2002 | Andreas et al. |
| 6,358,258 | B1 | 3/2002 | Arcia et al. |
| 6,387,105 | B1 | 5/2002 | Gifford, III et al. |
| 6,391,038 | B2 | 5/2002 | Vargas et al. |
| 2002/0082614 | A1 | 6/2002 | Logan et al. |

\* cited by examiner

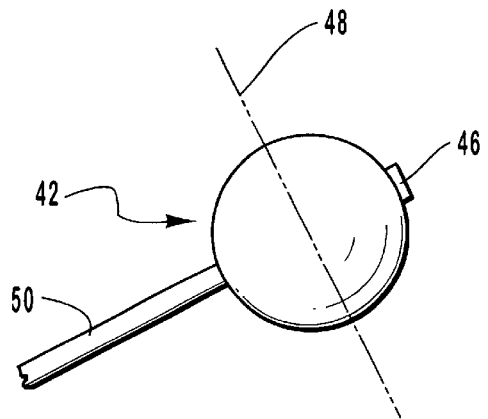
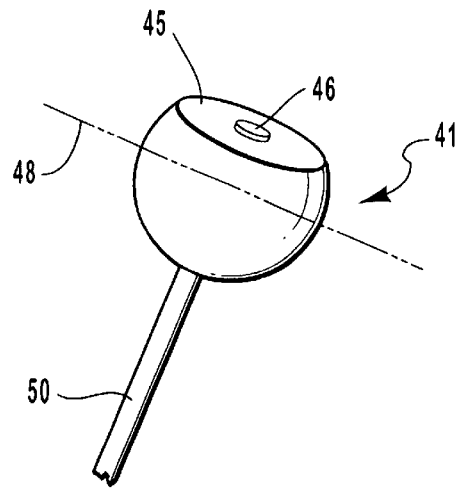
FIG. 5A  FIG. 5B
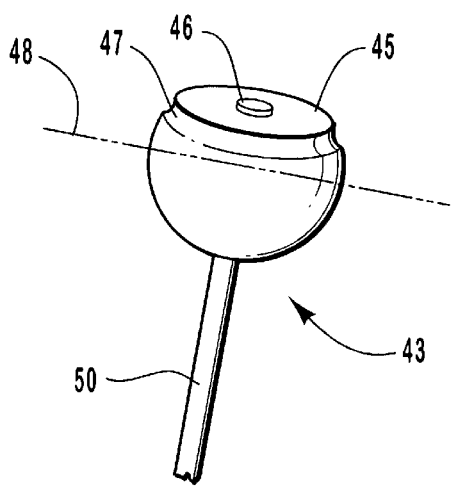
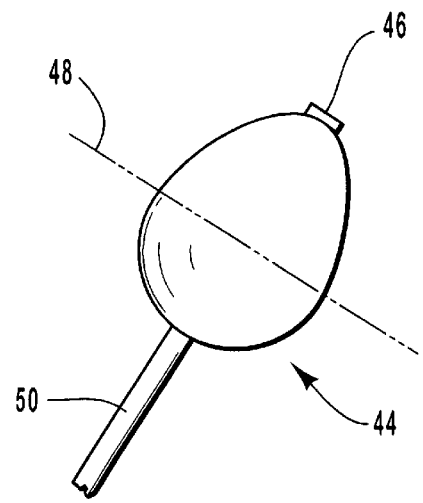
FIG. 5C  FIG. 5D

COMPRESSION PLATE ANASTOMOSIS APPARATUS

BACKGROUND OF THE INVENTION

1. The Field of the Invention

The present invention is directed generally to anastomosis methods, systems and devices. More specifically the present invention is directed to compression plate vascular anastomosis methods, systems and devices with the use of a vascular anvil.

2. Relevant Technology

Endoscopic applications are generally used in intracavity procedures such as intrathoracic and intraabdominal procedures. Peripheral techniques are usually employed in other body regions, such as arms and legs. It is desirable to be able to provide by active endoscopic or peripheral procedures a variety of medical services that are currently provided by techniques that are more invasive and more demanding in time and in medical resources and skills. This goal is justified by the efficiency, effectiveness, safety, low cost, and preventive accomplishments of active endoscopic or peripheral procedures. In particular, this invention provides new methods, devices and systems for performing vascular anastomoses by intraluminally directed active endoscopic or peripheral procedures. The intraluminally directed or intravascular part of the procedures of this invention is based on an examination performed by, for example, fluoroscopy, and extraluminal manipulation is performed endoscopically or according to a peripheral technique.

One aspect of this invention encompasses the quasi-simultaneity of the exploration, diagnosis and corrective tasks that can be achieved in vascular anastomoses performed by the active endoscopic or peripheral procedures of this invention. Another aspect of this invention includes the minimally invasive character of the vascular anastomoses that are performed by the active endoscopic or peripheral procedures of this invention. These procedures are also characterized by comparatively reduced requirements of medical facilities and skill. To more effectively describe and enable the present invention, a review of some basic terminology and related technology is offered in the immediately following subsections.

2.1. Terminology

An anastomosis is an operative union of two hollow or tubular structures. Anastomotic structures can be part of a variety of systems, such as the vascular system, the digestive system or the genitourinary system. For example, blood is shunted from an artery to a vein in an arteriovenous anastomosis, and from the right pulmonary artery to the superior vena cava in a cavopulmonary anastomosis. In other examples, afferent and efferent loops of jejunum are joined in a Braun's anastomosis after gastroenteroscopy; the ureter and the Fallopian tube are joined in a ureterotubal anastomosis, and the ureter and a segment of the sigmoid colon are joined in a ureterosigmoid anastomosis. In microvascular anastomosis, very small blood vessels are anastomosed usually under surgical microscope.

An anastomosis is termed end-to-end when the terminal portions of tubular structures are anastomosed, and it is termed end-to-side when the terminal portion of a tubular structure is anastomosed to a lateral portion of another tubular or hollow structure. In an end-to-side anastomosis, we often refer to the structure whose end is anastomosed as the "graft vessel" while the structure whose side wall is anastomosed is referred to as the "receiving structure".

Anastomotic material typically includes autologous material, but it can also include heterologous material or synthetic material. An autologous graft is a graft in which the donor and recipient areas are in the same individual. Heterologous material is derived from an animal of a different species. The graft can be made of a synthetic material such as expanded polytetrafluoroethylene ("ePTE"). Wolf Dieter Brittinger, Gottfried Walker, Wolf-Dieter Twittenhoff, and Norbert Konrad, Vascular Access for Hemodialysis in Children, Pediatric Nephrology, Vol. 11 (1997) pp. 87–95.

A nonocclusive anastomosis is typically an end-to-side anastomosis in which the flow of matter through the vessel that is anastomosed in its side is not interrupted while the anastomosis is performed. Most conventional techniques for vascular anastomosis require the interruption of blood flow through the receiving vessel while the anastomosis is performed.

Although the parts of a blood vessel are designated by well-known terms in the art, a few of these parts are briefly characterized here for introducing basic terminology. A blood vessel is in essence a tubular structure. In general, the region comprised within tubular walls, such as those defining a blood vessel or the walls defining the tubular member of an endoscope, is termed the lumen or the intraluminal space. A lumen that is not occluded is a patent lumen and the higher the patency of a blood vessel, the less disrupted the blood flow through such vessel is. A reduction of a blood vessel's patency can be caused by a stenosis, which is generally a stricture or narrowing of the blood vessel's lumen. A hyperplasia, or tissue growth, can also reduce a blood vessel's patency. Reduction of blood vessel patency, and in general a disruption in a vessel's blood flow, can lead to ischemia, which is a local lack of oxygen in tissue due to a mechanical obstruction of the blood supply.

A stent is a device that can be used within the lumen of tubular structures to assure patency of an intact but contracted lumen. Placement of a stent within an occluded blood vessel is one way of performing an angioplasty, which is an operation for enlarging a narrowed vascular lumen. Angioplasty and bypass are different ways for reestablishing blood supply, an operation that is called revascularization.

A blood vessel is composed of three distinct layers. From inside to outside, these layers include the intima, the media and the adventitia. The intima is a single layer of flat cells that collectively line the lumen. The media is a thick middle layer composed of smooth muscle cells. The adventitia is an outer layer that comprises fibrous covering.

Angiography is a technique for performing a radiograph of vessels after the injection of a radio-opaque contrast material. This technique usually requires percutaneous injection of a radio-opaque catheter and positioning under fluoroscopic control. An angiogram is a radiograph obtained by angiography. Fluoroscopy is an examination technique with an apparatus, the fluoroscope, that renders visible the patterns of X-rays which have passed through a body under examination.

2.2 Related Technology

The operative union of two hollow or tubular structures requires that the anastomosis be tight with respect to the flow of matter through such structures and also that the anastomosed structures remain patent for allowing an uninterrupted flow of matter therethrough. For example, anastomosed blood vessels should not leak at the anastomosis site, the anastomotic devices should not significantly disrupt the flow of blood, and the anastomosis itself should not cause a biological reaction that could lead to an obstruction of the anastomosed blood vessels. In particular, anastomosed blood vessels should remain patent and they should ideally not develop hyperplasia, thrombosis, spasms or arteriosclerosis.

Because anastomosed structures are composed of tissues that are susceptible to damage, the anastomosis should furthermore not be significantly detrimental to the integrity of these tissues. For example, injury to endothelial tissue and exposure of subintimal connective tissue should be minimized or even eliminated in vascular anastomosis.

Because structures to be anastomosed are internal, an anastomosis requires a degree of invasion. The invasive character of an anastomosis, however, should be minimized subject to the reliable performance of a satisfactory anastomosis. Accordingly, there has been a noticeable trend during the last quarter of this century towards less invasive surgical intervention, a surgical style that is termed minimally invasive surgery. This style is characterized by pursuing a maximal treatment effect with minimal damage to surrounding and overlying normal structures. In addition, successful minimally invasive procedures should procure patency and they should minimize damage to the tissues of the anastomosed structures themselves.

A plurality of factors provide a propitious environment for this trend towards minimally invasive surgery. These factors include the development of high-technology diagnostic devices, the innate characteristics of human psychology and economic imperatives.

High-technology diagnostic devices such as flexible fiber-optic endoscopes and intravascular catheters have considerably enhanced our ability for performing a reliable spacio-temporal location of disease. More specifically, these devices permit the early and accurate determination of disease processes and their loci. Furthermore, it is known that the earlier a tumor or growth can be identified, the more responsive it is to therapy by a minimally invasive technique. See Rodney Perkins, Lasers in Medicine in Lasers—Invention to Application, edited by John R. Whinnery, Jesse H. Ausubel, and H. Dale Langford, p. 104, National Academy of Engineering, National Academy Press, Washington, D.C. 1987. (This article will hereinafter be referred to as "Lasers—Invention to Application"). See also Edward R. Stephenson, Sachin Sankholkar, Christopher T. Ducko, and Ralph J. Damiano, Robotically Assisted Microsurgery for Endoscopic Coronary Artery Bypass Grafting, Annals of Thoracic Surgery, Vol. 66 (1998) p. 1064. (This article will hereinafter be referred to as "Endoscopic Coronary Artery Bypass Grafting").

Human psychology also contributes to the growing trend towards minimally invasive techniques. This is attributed to the accepted prevailing preference of a minimally invasive technique with respect to a more invasive surgical technique whenever the outcomes of these two techniques are equivalent.

Finally, minimally invasive techniques are generally cost effective to insurers and to society in general because they are performed on an outpatient basis or else they require comparatively shorter hospitalization time. Furthermore, the less tissue is invasively effected in a procedure, the more likely it is that the patient will recover in a comparatively shorter period of time with lower cost hospitalization. Therefore, economic factors also favor the development of minimally invasive techniques because they can be performed with lower morbidity risk and they satisfy economic imperatives such as reduced cost and reduced loss of productive time. See Rodney Perkins in Lasers—Invention to Application, p. 104; Endoscopic Coronary Artery Bypass Grafting, pp. 1064, 1067.

Particularly in the field of vascular anastomosis, it is acknowledged that there is an increasing demand for an easier, quicker, less damaging, but reliable procedure to create vascular anastomosis. This demand is further revitalized by the movement of vascular procedures towards minimally invasive procedures. See Paul M. N. Werker and Moshe Kon, Review of Facilitated Approaches to Vascular Anastomosis Surgery, Annals of Thoracic Surgery, Vol. 63 (1997) pp. S122–S127. (This work will hereinafter be referred to as "Review of Facilitated Approaches to Vascular Anastomosis").

Conventional exploration and anastomosis techniques are not always implemented in such a way as to satisfy the demand for an easier, quicker, less damaging, but reliable vascular anastomosis. The following overview of conventional exploration and anastomosis techniques closes this background section on related technology.

Exploration of a blood vessel typically provides necessary information for locating and diagnosing vascular abnormalities such as those that reduce vascular patency. This exploration can rely on examination techniques such as angiography and endoscopy. Vascular abnormalities are usually detected fluoroscopically according to an angiography procedure. When it is concluded that the appropriate corrective action requires an anastomosis, conventional procedures ordinarily follow a sequence in which the anastomosis is not performed at the time when the initial exploration and diagnostic are performed, but at a later time and in a typically different clinical setup. Accordingly, the time and resources that are spent during the exploration and diagnostic phases are not directly employed in the performance of an appropriate corrective action, such as an anastomosis.

By performing an anastomosis considerably after the initial exploration has taken place and in a different location and clinical environment, these conventional procedures also waste a significant part of the information acquired at the exploration phase. Images obtained during an angiographic procedure are typically recorded on film or digital medium. In current clinical practice, these recorded images are reviewed in a subsequent clinical setting and based upon a knowledge of external anatomy, the lesion location and optimal site for anastomosis are estimated. This process sacrifices potentially useful information. Fluoroscopic visualization is no longer available without repeating the angiogram procedure, and in conventional practice external anatomic localization is used in correlation with previously recorded images. In addition to this external inspection, conventional procedures could rely on imaging for determining the optimal anastomosis site when corrective action is taken. However, having to reacquire information leads to a waste of resources, it significantly increases the period of time from exploration to corrective action, it is an additional burden on the patient, and it enhances the invasive character of the treatment that is administered to the patient. Furthermore, reacquisition of information might have to be done in an environment that demands higher skills and more resources than they would have been otherwise needed. For example, the opening of a body cavity to expose the anatomical region around a potential anastomosis site, the determination of the optimal anastomosis site by external inspection, and the surgical performance of the anastomosis are part of a treatment that is more complex, requires practitioners with more training, and may be more time and resource consuming than the treatment provided by the methods, systems and apparatuses of the present invention.

Vascular anastomosis techniques can be classified in a plurality of groups. Although with various degrees of success, all these techniques generally intend to provide leak-proof joints that are not susceptible to mechanical failure, and they also intend to minimize damage and reduce the undesirable effects of certain operational features that may lead to post-anastomosis complications. Damage to be minimized and operational features whose undesirable effects should be reduced include endothelial coverage injury, exposure of subintimal connective tissue, exposure of an intraluminal foreign component, blood flow interruption, irregularities at the junction, adventitial tissue stripping, intimal injury, installment of a foreign rigid body, use of materials that may have toxic effects, damage to surrounding tissue, extensive vessel eversion, and tissue plane malalignment. Post-anastomosis complications include intimal hyperplasia, atherosclerosis, thrombosis, stenosis, tissue necrosis, vascular wall thinning, and aneurism formation. In addition, vascular anastomosis techniques are characterized by varying abilities to successfully cope with the dilating character of the structures to be anastomosed, their diversity in size, and the possibility that at least one structure may grow after the anastomosis has been performed. Other variables that partially determine the suitability of a specific anastomosis technique include the nature of the material to be anastomosed (for example, autologous, heterologous, or synthetic), the desired reduction in operative time, the skill requirements, and the healing time.

Each one of the techniques discussed hereinbelow for joining anastomosed structures presents a compromise for reducing undesirable effects in the practice of vascular anastomosis. High standards in one or a few aspects of the anastomosis can sometimes be achieved only at the expense of sacrificing what otherwise would have been the benefits of other aspects of the anastomosis.

Since early in the 20th century when vessel anastomoses were performed with an acceptable degree of reliability, the standard for creation of a vascular anastomosis has been manual suturing. Review of Facilitated Approaches to Vascular Anastomosis, p. S122. Suturing devices and methods are still being developed with the aim at performing less invasive surgical procedures within a body cavity. See, for example, U.S. Pat. No. 5,860,992 disclosing devices and methods for suture placement while performing less invasive procedures.

Regarding the application of sutures in vascular anastomoses, it has been generally reported that "the insertion of transmural stitches, even in experienced hands that employ atraumatic techniques and fine sutures, causes significant damage to the vessel wall. As the result of this the subendothelial matrix becomes exposed to the bloodstream and initiates the formation of a thrombus. The same process takes place at the actual site of the anastomosis in the case of intima-intima apposition. These processes are multifactorial but can cause obstruction of the complete anastomosis, especially in small vessels." Review of Facilitated Approaches to Vascular Anastomosis, p. S122. In addition to proximal occlusion, needle-and-suture-mediated intimal penetration is believed to represent a source of platelet emboli, which can cause distal embolization and thus a hazard in brain revascularization and myocardial circulation. Patrick Nataf, Wolff Kirsch, Arthur C. Hill, Toomas Anton, Yong Hua Zhu, Ramzi Ramadan, Leonardo Lima, Alain Pavie, Christian Cabrol, and Iradj Gandjbakhch, Nonpenetrating Clips for Coronary Anastomosis, Annals of Thoracic Surgery, Vol. 63 (1997) p. S137. (This article will hereinafter be referred to as "Nonpenetrating Clips for Coronary Anastomosis"). Furthermore, it is considered that "suture anastomosis of small vessels is time-consuming and tedious and demands a long and continuous training if high patency rates are to be regularly achieved." Willy D. Boeckx, Oliskevigius Darius, Bert van den hof, and Carlo van Holder, Scanning Electron Microscopic Analysis of the Stapled Microvascular Anastomosis in the Rabbit, Annals of Thoracic Surgery, Vol. 63 (1997) p. S128. (This work will hereinafter be referred to as "Microscopic Analysis of Stapled Microvascular Anastomosis"). In contrast, in all specialties that employ vascular surgery, "there is an increasing demand for a simple, time-saving, but reliable automated, semiautomated, or at least facilitated method to replace the process of manually sutured anastomosis. The most important reason for this demand is the movement of cardiac bypass surgery toward a minimally invasive and possibly even an endoscopic procedure." Review of Facilitated Approaches to Vascular Anastomosis, p. S122. In this respect, improvement "may come from techniques that do not lead to exposure of [a] damaged vessel wall to the bloodstream." Id., p. S122.

Besides the group that includes techniques which rely on suturing, vascular anastomosis techniques can generally be classified in four groups depending on how the tissue is joined and on the type of device or material used for joining the tissue of the anastomosed vessels. These groups are: Stapling and clipping techniques, coupling techniques, pasting techniques, and laser techniques. Id., pp. S122–S127.

2.2.1. Stapling and clipping techniques

Although some staplers have been reported as providing leaky joints, a variety of staplers have been developed for end-to-end and for end-to-side anastomosis. U.S. Pat. No. 5,366,462 discloses a method of end-to-side vascular anastomosis. According to this method, the end of the graft blood vessel that is to be anastomosed is everted by 180°; one end of the staple pierces both vessels with punctures exposed to the blood flow and the other end of the staple pierces the outside of the receiving vessel. U.S. Pat. No. 5,732,872 discloses a surgical stapling instrument that comprises an expandable anvil for aiding in the stapling of a 180° everted end of a graft vessel to a receiving vessel. This patent also discloses a stapling instrument for joining the 180° everted second end of a graft vessel whose opposite end has already been anastomosed. To anastomose this second end, this technique requires clearance around the area in which the anastomosis is performed, exposure of the receiving blood vessel, external anatomic identification, and significant external manipulation in the open area around the anastomosis site. U.S. Pat. No. 4,930,674 discloses methods of end-to-end and end-to-side anastomosis and a surgical stapler that comprises a vessel gripping structure for joining the 180° everted end of a graft vessel to another vessel. U.S. Pat. No. 5,695,504 discloses methods and a system for performing an end-to-side vascular anastomosis, where the system is applicable for performing an anastomosis between a vascular graft and the ascending aorta in coronary artery bypass surgery, particularly in port-access coronary artery bypass graft surgery. This system includes a staple with a configuration that combines the functions of an anchor member and a coupling member into a one-piece anastomosis staple. U.S. Pat. No. 5,861,005 discloses an arterial stapling method and device for stapling an opening in an anatomical structure, whether the opening is deliberately formed or accidentally caused. This device employs a balloon catheter that helps positioning the stapling mechanism properly on the organ to be stapled.

Some stapling devices rely on access to the anastomosis area through an opening that might be as big as or comparable to typical openings that are required in surgical procedures. Furthermore, the 180° eversion of vessel ends is viewed as an operation that can be difficult, particularly in sclerotic vessels. Review of Facilitated Approaches to Vascular Anastomosis, p. S123.

In general, clipping techniques rely on arcuate legged clips for achieving a flanged, nonpenetrated, intimal approximation of the anastomosed structures. Reportedly, the use of clips leads to a biologically and technically superior anastomosis as compared to the penetrating microsuture. Review of Facilitated Approaches to Vascular Anastomosis, p. S123. By approximating the everted walls of the two vessels to be anastomosed, a clipping technique avoids stitching and reportedly the subsequent risk of intimal hyperplasia. Gianfranco Lisi, Louis P. Perrault, Philippe Menasche, Alain Bel, Michel Wassef, Jean-Paul Vilaine, and Paul M. Vanhoutte, Nonpenetrating Stapling: A Valuable Alternative to Coronary Anastomoses, Annals of Thoracic Surgery, Vol. 66 (1998) p. 1707. In addition, maintenance of an uninjured endothelial coverage and avoidance of exposure of subintimal connective tissue are considered important features because "regenerated endothelium presents selective dysfunction that may predispose to spasm and atherosclerosis, thereby affecting both medium-term and long-term graft patency" and the risk of thrombosis at the anastomotic site can be reduced. Id., p. 1707.

Nonpenetrating vascular closure staples ("VCS") have been used in anastomoses performed to provide access for dialysis, as well as in kidney and pancreas transplantation. It has been concluded in light of these anastomoses that "the fact that VCS staples are interrupted and do not disrupt the endothelium or have an intraluminal component makes them ideal" for achieving the goals of kidney transplantation. V. E. Papalois, J. Romagnoli, and N. S. Hakim, Use of Vascular Closure Staples in Vascular Access for Dialysis, Kidney and Pancreas Transplantation, International surgery, Vol. 83 (1998) p. 180. These goals include the avoidance of postoperative thrombosis and the avoidance of renal artery stenosis. As with kidney transplants, no anastomotic abnormalities were detected in pancreatic transplants, where the avoidance of arterial stenosis is also very important. Id., p. 180. The results of anastomoses performed for providing vascular access for dialysis were also reported successful. Id., p. 179. In addition, it has been reported that the "VCS applier is easy to manipulate, is as safe as hand-suture methods, and has time saving potential. VCS clips are useful for vascular anastomoses of blood access." Hiroaki Haruguchi, Yoshihiko Nakagawa, Yasuko Uchida, Junichiro Sageshima, Shohei Fuchinoue and Tetsuzo Agishi, Clinical Application of Vascular Closure Staple Clips for Blood Access Surgery, ASAIO Journal, Vol. 44(5) (1998) pp. M562–M564.

In a study of microvascular anastomosis of rabbit carotid arteries, some anastomosis were stapled using nonpenetrating 0.9 mm microclips and some anastomosis were conventionally sutured. Arcuate-legged, nonpenetrating titanium clips are applied according to a clipping technique in an interrupted fashion to everted tissue edges at high compressive forces. It is considered that this technique "enables rapid and precise microvascular reconstructions, but requires both training and evertable tissue walls." Nonpenetrating Clips for Coronary Anastomosis, Annals of Thoracic Surgery, p. S135. An example of this clip applier is the VCS device, Autosuture, United States Surgical Corporation, Norwalk, Conn. Nonpenetrating Clips for Coronary Anastomosis, pp. S135–S137. U.S. Pat. No. 5,702,412 discloses a method and devices for performing end-to-side anastomoses where the side wall of one of the structures is cut from the intraluminal space of the graft vessel and the anastomosed structures can be secured by a plurality of clips or by suturing.

It has been concluded that stapled microvascular anastomosis is fast and reliable and histomorphologic examination of the anastomotic site revealed no major differences between sutured and stapled groups. Microscopic Analysis of Stapled Microvascular Anastomosis, p. S128. Furthermore, it has also been reported that the "clipped anastomotic technique has a rapid learning curve, the same safety as suture methods, and the potential for facilitating endoscopic vascular reconstruction." Nonpenetrating Clips for Coronary Anastomosis, p. S135. In a study undertaken to compare VCS clips with sutured arterial end-to-end anastomosis in larger vessels, it was concluded that this type of anastomosis "can be performed more rapidly with VCS clips than continuous sutures", and that VCS clips "are potentially useful situations where the clamp time of the vessel is critical." Emmanouil Pikoulis, David Burris, Peter Rhee, Toshiya Nishibe, Ari Leppaniemi, David Wherry and Norman Rich, Rapid Arterial Anastomosis with Titanium Clips, The American Journal of Surgery, Vol. 175 (1998) pp. 494–496.

Nevertheless, clipping may lead to irregularities at the junction of the anastomosed vessels. In addition, it has been reported that "both periadventitial tissue stripping and microvascular clip application have deleterious effects in the early postoperative period" and that "temporary clips with a lesser width must be used in place of microvascular clips" while performing microvascular anastomosis. S. Keskil, N. Ceviker, K. Baykaner, Ö. Uluoǧlu and Z. S. Ercan, Early Phase Alterations in Endothelium Dependent Vasorelaxation Responses Due to Aneurysm Clip Application and Related Manipulations, Acta Neurochirurgica, Vol. 139(1) (1997) pp. 71–76.

2.2.2. Coupling

Tissue bonding by coupling with the aid of devices such as stents, ferrules, or rings without staples is considered to be older than stapling. Among the more recent devices and techniques, U.S. Pat. No. 4,523,592 discloses anastomotic coupling means capable of end-to-end and end-to-side anastomosis without resorting to suturing. The vessels are coupled with a pair of coupling disc members that cooperatively lock and secure the everted tissue from the anastomosed structures. These everted tissues remain in intima-intima contact with no foreign material exposed to the lumen of the anastomosed vessels. U.S. Pat. Nos. 4,607,637, 4,917,090 and 4,917,091 also disclose the use of anastomosis rings and an instrument for joining vessels or tubular organs which are threaded to the annular devices before the joining. The instrument and the anastomosis rings are shaped and adapted to be utilized mainly in microsurgery. U.S. Pat. Nos. 4,657,019 and 4,917,087 disclose devices, kits and methods for non-suture end-to-end and end-to-side anastomosis of tubular tissue members that employ tubular connection members and provide intima-intima contact at the anastomosis site with no foreign material exposed to the lumen of the vessels being joined. An annuli pair that provides an anastomotic clamp and that is especially adapted for intraluminal disposition is disclosed in U.S. Pat. No. 5,336,233. Because of the intraluminal disposition, this device is exposed to the blood flow in the anastomosed vessels. U.S. Pat. No. 4,907,591 discloses a surgical instrument for use in the installation of an assembly of interlocking coupling members to achieve compression anastomosis of tubular structures. Other coupling devices include the use of intraluminal soluble stents and extraluminal glues, such as cyanoacrylates, for creating nonsuture anastomoses. Reportedly, 98% patency was obtained with these soluble polyvinyl alcohol stents. Review of Facilitated Approaches to Vascular Anastomosis, pp. S124–S125. An absorbable anastomotic device for microvascular surgery relies on the cuffing principle with injection-molding techniques using the polymer polyglactin. Vessel ends that are everted 180° are joined in this technique by an interconnecting collar so that an intima-intima seal is achieved. Reportedly, 96% patency was obtained with these absorbable interconnecting collars. Review of Facilitated Approaches to Vascular Anastomosis, p. S125.

The major advantage of a coupling microvascular anastomotic device has been reported to be the reduction in the time needed for a venous anastomosis, which decreases the total ischemic time. Maisie L. Shindo, Peter D. Constantino, Vincent P. Nalbone, Dale H. Rice and Uttam K. Sinha, Use of a Mechanical Microvascular Anastomotic Device in Head and Neck Free Tissue Transfer, Archives of Otolaryngology—Head & Neck Surgery, Vol. 122(5) (1996) pp. 529–532. Although a number of coupling techniques do not place any foreign body in the intraluminal space of the anastomosed vessels, it is considered that the use of a foreign rigid body such as a ring that encloses a dynamically dilating structure is a disadvantage of this type of technique. Furthermore, this type of technique is viewed as not being flexible enough for its application to significant vessel size discrepancies in end-to-side anastomosis, and the devices are characterized as being of limited availability and needed in sets of different sizes. Microscopic Analysis of Stapled Microvascular Anastomosis, p. S128. In addition, most coupling techniques require considerable eversion, incisions and mounting of the coupling devices that are difficult or impossible to apply endoscopically.

2.2.3. Adhesives

Pasting by applying adhesives or glues is widely employed in medicine. Several glues have been tested in anastomotic procedures, including fibrin glue, cyanoacrylic glues and photopolymerizable glues.

Fibrin glue is a biological two-component sealant comprising fibrinogen solution and thrombin combined with calcium chloride solution. These components are typically available deep-frozen in preloaded syringes, and they are mixed during application after thawing. Commercially available fibrin glue Tissucol has reportedly been approved by the Food and Drug Administration for use in the United States. See, Thomas Menovsky and Joost de Vries, Use of Fibrin Glue to Protect Tissue During $CO_2$ Laser Surgery, Laryngoscope Vol. 108 (1998) pp. 1390–1393. This article will hereinafter be referred to as "Fibrin Glue in Laser Surgery."

The use of fibrin glue has been found to be practical in telescoping anastomoses and in microanastomoses. Satoru Saitoh and Yukio Nakatsuchi, Telescoping and Glue Technique in Vein Grafts for Arterial Defects, Plastic and Reconstructive Surgery, Vol. 96(6) (1995) pp. 1401–1408; Seung-Kyu Han, Sung-Wook Kim and Woo-Kyung Kim, Microvascular Anastomosis With Minimal Suture and Fibrin Glue: Experimental and Clinical Study, Microsurgery, Vol. 18(5) (1998) pp. 306–311. In contrast, it has been reported that the application of thrombin-based fibrin sealant (fibrin glue) to microvascular anastomoses can have noticeable deleterious effects, particularly when used in venous anastomosis. Christopher A. Marek, Lester R. Amiss, Raymond F. Morgan, William D. Spotnitz and David B. Drake, Acute Thrombogenic Effects of Fibrin Sealant on Microvascular Anastomoses in a Rat Model, Annals of Plastic Surgery, Vol. 41(4) (1998) pp. 415–419.

A biological procoagulant solution has been described as promising. The mixture contains bovine microfibrillar collagen and thrombin. Gary Gershony, John M. Brock and Jerry S. Powell, Novel Vascular Sealing Device for Closure of Percutaneous Vascular Access Sites, Catheterization and Cardiovascular Diagnosis, Vol. 45(1) (1998) pp. 82–88; Ted Feldman, Percutaneous vascular Closure: Plugs, Stitches, and Glue, Catheterization and Cardiovascular Diagnosis, Vol. 45(1) (1998) p. 89; Zoltan G. Turi, Plugging the Artery With a Suspension: A Cautious Appraisal, Catheterization and Cardiovascular Diagnosis, Vol. 45(1) (1998) pp. 90–91.

Cyanoacrylic glues tested on vessels include methyl cyanoacrylate and butyl cyanoacrylate, such as Histoacryl glue (butyl-2-cyanoacrylate). The ultra-violet polymerizable glue polyethyleneglycol 400 diacrylate has also been tested and reported that it "is able to effectively seal vessel puncture sites and anastomotic junctions without acutely augmenting local vascular thrombogenicity." G. A. Dumanian, W. Dascombe, C. Hong, K. Labadie, K. Garrett, A. S. Sawhney, C. P. Pathak, J. A. Hubbell and P. C. Johnson, A new Photopolymerizable Blood Vessel Glue That Seals Human Vessel Anastomoses Without Augmenting Thrombogenicity, Plastic and Reconstructive Surgery, Vol. 95(5) (1995) pp. 901–907.

Glues used in anastomotic practice face the challenges inherent to factors that include toxicity, thrombogenicity, vascular wall thinning, and mechanical strength of the joint. Review of Facilitated Approaches to Vascular Anastomosis, p. S125; Henk Giele, Histoacryl Glue as a Hemostatic Agent in Microvascular Anastomoses, Plastic and Reconstructive Surgery, Vol. 94(6) (1994) p. 897.

2.2.4. Lasers

Lasers have been used in angioplastic revascularization since about 1984. See for example, Markolf H. Niemz, Laser Tissue Interactions, pp. 216–221, Springer Verlag 1996, (this work will hereinafter be referred to as "Laser Tissue Interactions"); R. Viligiardi, V. Gallucci, R. Pini, R. Salimbeni and S. Galiberti, Excimer Laser Angioplasty in Human Artery Disease, in Laser Systems in Photobiology and Photomedicine, edited by A. N. Chester, S. Martellucci and A. M. Scheggi, pp. 69–72, Plenum Press, New York, 1991; Timothy A. Sanborn, Laser Angioplasty, in Vascular Medicine, edited by Joseph Losealzo, Mark A. Creager and Victor Brounwald, pp. 771–787, Little Brown Co. Whereas balloon angioplasty typically fractures, compresses or displaces plaque material, laser angioplasty typically removes plaque material by vaporizing it. Lawrence I. Deckelbaum, Cardiovascular Applications of Laser Technology, in Laser Surgery and Medicine, edited by Carmen A. Puliafito, pp. 1–27, Wiley-Liss, 1996.

The refinement of anastomosis techniques that rely on laser has been progressing since the reportedly first use of a neodymium yttrium-aluminum-garnet laser ("Nd-YAG laser") on vascular anastomosis in 1979. Particularly in an end-to-side vascular anastomosis, the end of a graft in the form of a tubular structure is connected to the side wall of a receiving vessel so that the anastomosed end of the graft encompasses the anastomosis fenestra, or artificial window, that has been formed into the side wall of the receiving vessel. Consequently, lasers can be used in anastomoses for welding the anastomosed structures and/or for opening the anastomosis fenestra. In addition to YAG lasers, such as Nd-YAG and Ho-YAG lasers, Excimer, diode, $CO_2$ and argon lasers have also been used in vascular anastomoses.

Laser welding has been defined as the process of using laser energy to join or bond tissues. Typically, laser welding relies on photothermal effects, but efforts are being made to develop laser welding that relies on photochemical effects, where the laser radiation activates cross-linking agents that are expected to produce stronger links than those produced by photothermal welding. Lawrence S. Bass and Michael R. Treat, Laser Tissue Welding: A Comprehensive Review of Current and Future Clinical Applications, in Laser Surgery and Medicine, edited by Carmen A. Puliafito, pp. 381–415. (This work will hereinafter be referred to as "Laser Tissue Welding").

Generally, the use of lasers in anastomotic practice faces the challenges inherent to factors that include the cost of laser purchase, maintenance and training, radiation damage to surrounding tissue, aneurism formation, the need for about three or four sutures (versus the nine or ten sutures applied in conventional anastomosis), side effects of heat-induced tissue welding, and mechanical failure at the anastomosis site. Review of Facilitated Approaches to Vascular Anastomosis, pp. S125–S126; Laser Tissue Welding, pp. 407–410; Brian C. Cooley, Heat-Induced Tissue Fusion For Microvascular Anastomosis, Microsurgery, Vol 17(4) (1996) pp. 198–208. It has been reported, however, that the "nonocclusive Excimer laser-assisted anastomosis technique is safe and yields a high long-term patency rate in neurosurgical patients" and that there might be indications for this method in coronary bypass surgery. Cornelis A. F. Tulleken, Rudolf M. Verdaasdonk, and Hendricus J. Mansvelt Beck, Nonocclusive Excimer Laser-Assisted End-to-Side Anastomosis, Annals of Thoracic Surgery, Vol.63 (1997) pp. S138–S142. (This article will hereinafter be referred to as "Nonocclusive Excimer Laser-Assisted End-to-Side Anastomosis"). In addition, laser anastomosis is considered to offer moderately reduced operative time, reduced skill requirements, faster healing, ability to grow, and possibly reduced intimal hyperplasia. Laser Tissue Welding, pp. 407–410 (further reporting on selected microvascular anastomosis studies with lasers that include $CO_2$, argon, and diode lasers). Furthermore, research is being done to replace some of the initial laser sources by other lasers that are believed to be more suitable for clinical applications. For example, recent work with the 980 nm diode laser indicates that it may "replace in the near future laser sources of older conception such as the Nd-YAG." W. Cecchetti, S. Guazzieri, A. Tasca and S. Martellucci, 980 nm High Power Diode Laser in Surgical Applications, in Biomedical Optical Instrumentation and Laser-Assisted Biotechnology, edited by A. M. Verga Scheggi, S. Martellucci, A. N. Chester and R. Pratesi, pp. 227–230, Kluwer Academic Publishers, Dordrecht, The Netherlands, 1996.

The $CO_2$ laser can seal blood vessels, including small blood vessels of about 0.5 mm in diameter or less and it has been used in microvascular anastomosis such as in human lympho-venous anastomosis. D. C. Dumitras and D. C. A. Dutu, Surgical Properties and Applications of Sealed-off $CO_2$ Lasers, in Biomedical Optical Instrumentation and Laser-Assisted Biotechnology, edited by A. M. Verga Scheggi, S. Martellucci, A. N. Chester and R. Pratesi, pp. 231–239, Kluwer Academic Publishers, Dirdrecht, The Netherlands, 1996. In addition to the $CO_2$ laser which is an efficient vaporizer of tissue, other lasers that effectively vaporize tissue include the argon and the KTP/532 lasers. Lasers—Invention to Application, p.106.

The argon laser has been reported to offer advantages over conventional end-to-end anastomosis procedures applied to growing vessels. Eiji Chikamatsu, Tsunehisa Sakurai, Naomichi Nishikimi, Takashi Yano and Yuji Nimura, Comparison of Laser Vascular Welding, Interrupted Sutures, and Continuous Sutures in Growing Vascular Anastomoses, Lasers in Surgery and Medicine, Vol. 16(1) (1995) pp. 34–40. It has also been reported that low temperature argon laser welding limits anastomotic thrombogenicity, which is thought of as a factor that may improve early patency of venous and small arterial bypass grafts. Steven B. Self, Douglas A. Coe and James M. Seeger, Limited Thrombogenicity of Low Temperature Laser-Welded Vascular Anastomoses, Lasers in Surgery and Medicine, Vol. 18(3) (1996) pp. 241–247.

The use of laser for medical purposes requires safety measures for protecting health care practitioners who handle the laser device and for shielding surrounding tissues and avoiding unintended radiation induced damage. Laser shield materials include layers of polymethylmethacrylate and tinfoil. See, Christine C. Nelson, Krystyna A. Pasyk and Gregory L. Dootz, Eye Shield for Patients Undergoing Laser Treatment, American Journal of Ophthalmology Vol. 110 (1990) pp. 39–43. Laser shield materials are known and they have been disclosed in a variety of sources such as Alex Mallow and Leon Chabot, Laser Safety Handbook, Van Nostrand Reinhold Co., New York (1978), and A. Roy Henderson, A Guide to Laser Safety, Chapman & Hall, London (1997). In particular, for example, the biological sealant fibrin glue can prevent severe damage to tissue when accidentally exposed to $CO_2$ laser radiation and intraoperative coating with fibrin glue can serve as a shield to protect arteries, veins, and nerves from accidental $CO_2$ laser exposure. Furthermore, it is considered that the use of fibrin glue for laser radiation protective processes "is especially attractive in . . . fields in which the glue is already used for sealing." Fibrin Glue in Laser Surgery at p. 1393.

2.2.5. Other devices and techniques

It is known that some anastomosis techniques combine different approaches. For example, biological glues that are based on proteins and other compounds are combined with laser radiation in laser soldering. "Laser soldering is a bonding technique in which a proteinaceous solder material is applied to the surfaces to be joined followed by application of laser light to seal the solder to the tissue surfaces." Laser Tissue Welding, pp. 389–392. Egg albumin, heterologous fibrin glue, and human albumin have been used as laser solders, also known as adjuvant materials for laser tissue welding. Dix P. Poppas, Theodore J. Choma, Christopher T. Rooke, Scott D. Klioze and Steven M. Schlossberg, Preparation of Human Albumin Solder for Laser Tissue Welding, Lasers in Surgery and Medicine, Vol. 13(5) (1993) pp. 577–580.

In an even newer technique, a chromophore is added to the solder to achieve photoenhancement effects that lead to an enhanced light absorption in the solder and not in the nontargeted tissue. Id., p. 391. In laser sealing, also known as laser-activated tissue sealing, sutured or stapled repairs are reinforced with laser solder, which is expected to provide "the strength and security of sutures and the watertightness of solder." Id., pp. 403–404.

The graft in a vascular anastomosis does not necessarily have to be an autologous blood vessel. In addition to ePTFE tubular grafts that have been referred to in a preceding subsection, several synthetic materials for vascular grafts have been used or are being developed.

Synthetic biomaterials that are being developed include polymeric materials with the proteins elastin and fibronectin. A. Maureen Rouhi, Contemporary Biomaterials, Chemical & Engineering News, Vol. 77(3) (1999) pp. 51–63.

ePTFE has been used with a variety of coatings. One type of coating includes fibrin glue that contains fibroblast growth factor type 1 and heparin. John L. Gray, Steven S. Kang, Gregory C. Zenni, Dae Un Kim, Petre I. Kim, Wilson H. Burgess, William Drohan, Jeffrey A. Winkels, Christian C. Haudenschild and Howard P. Greisler, FGF-1 Affixation Stimulates ePTFE Endothelialization without Intimal Hyperplasia, Journal of Surgical Research, Vol. 57(5) (1994) pp. 596–612; Joseph I. Zarge, Vicki Husak, Peter Huang and Howard P. Greisler, Fibrin Glue Containing Fibroblast Growth Factor Type 1 and Heparin Decreases Platelet Deposition, The American Journal of Surgery, Vol. 174(2) (1997) pp. 188–192; Howard P. Greisler, Claire Gosselin, Dewei Ren, Steven S. Kang and Dae Un Kim, Biointeractive Polymers and Tissue Engineered Blood Vessels, Biomaterials, Vol. 17(3) (1996) pp. 329–336. Another coating contains basic fibroblast growth factor in fibrin glue. M. Lanzetta, D. M. Crowe and M. J. Hickey, Fibroblast Growth Factor Pretreatment of 1-mm PTFE Grafts, Microsurgery, Vol. 17(11) (1996) pp. 606–611.

Other grafts comprise a synthetic biodegradable tubular scaffold, such as a vessel made of polyglactin/polyglycolic acid, that has been coated with autologous cells from a tissue culture. Toshiharu Shinoka, Dominique Shum-Tim, Peter X. Ma, Ronn E. Tanel, Noritaka Isogai, Robert Langer, Joseph P. Vacanti and John E. Mayer, Jr., Creation of Viable Pulmonary Artery Autografts Through Tissue Engineering, The Journal of Thoracic and Cardiovascular Surgery, Vol. 115(3) (1998) pp. 536–546.

A common feature of most conventional stapling, coupling and clipping techniques, particularly when applied to small-diameter vessels, is that they require a temporary interruption of the blood stream in the recipient vessel, a disruption that is thought to be not very well tolerated in cardiac bypass surgery. Review of Facilitated Approaches to Vascular Anastomosis, p. S126. In revascularization procedures of the brain, temporary occlusion of a proximal brain artery may cause brain ischemia, and consequently a nonocclusive anastomosis technique is required. Nonocclusive Excimer Laser-Assisted End-to-Side Anastomosis, p. 141. As the instrumentation that is needed at the anastomosis site becomes complex and cumbersome, a wider open area is needed for accessing the anastomosis site, thus leading to an increasingly invasive procedure. Furthermore, conventional anastomosis techniques are usually performed at a site that is determined by external observation of the affected area. This observation is performed at a time and in a medical setup that are different from the time and medical setup of a previous exploratory or diagnosis procedure.

Techniques that require the perforation of blood vessel tissue have raised concerns regarding intimal injury, adventitial stripping, tissue plane malalignment, and anastomotic bleeding. In addition, techniques that rely on devices that are exposed to the blood flow may lead to technical problems associated with a persistent intraluminal foreign body. These factors are thought to "contribute to both early and late anastomotic failure, particularly in the form of neointimal hyperplasia." Nonpenetrating Clips for Coronary Anastomosis, p. S135.

The need for completely endoscopic anastomosis procedures has been clearly expressed in the context of coronary artery bypass grafting. For example, it is currently acknowledged that "the goal of a completely endoscopic coronary artery bypass procedure has not yet been realized, and will require further technological advances." Endoscopic Coronary Artery Bypass Grafting, p. 1064. Furthermore, totally endoscopic coronary artery bypass grafting "is perceived by many as the ultimate surgical model of minimally invasive coronary artery bypass grafting". Hani Shennib, Amr Bastawisy, Michael J. Mack, and Frederic H. Moll, Computer-Assisted Telemanipulation: An Enabling Technology for Endoscopic Coronary Artery Bypass, Annals of Thoracic Surgery, Vol. 66 (1998) p. 1060.

Minimally invasive vascular grafting according to a peripheral procedure is equally desirable, and minimally invasive active endoscopic or peripheral methods, systems and devices are specially desirable. In addition, methods, systems and devices that can be used in catheter directed as well as in non-catheter directed vascular anastomosis are particularly desirable because sometimes an occluded or damaged vessel does not permit catheterization from a point that is too far from the anastomosis site.

These methods, systems and apparatuses are specially desirable when, in particular, they are versatile enough as to be able to incorporate a plurality of the desirable features that have been discussed hereinabove while reviewing different groups of vascular anastomosis techniques. This desirability is consistent with the reported expectation that reliable methods for facilitated anastomosing of vessels will be developed by combining the best features of a variety of techniques. Review of Facilitated Approaches to Vascular Anastomosis, p. S126.

Each one of the afore-mentioned patents and publications is hereby incorporated by reference in its entirety for the material disclosed therein.

OBJECTS AND BRIEF SUMMARY OF THE INVENTION

Conventional vascular anastomosis techniques do not rely on intraluminally assisted active endoscopic or peripheral procedures. It is therefore desirable to provide methods, systems and devices for their implementation as intraluminally assisted active endoscopic or peripheral procedures in vascular anastomosis.

An object of the present invention is to provide methods, systems, and devices for performing a minimally invasive anastomosis by directly relying on the information acquired at the time of performing an initial angiographic exploration.

Another object of this invention is to provide methods, systems, and devices such that the minimally invasive anastomosis is performed with devices that can be utilized under an active endoscopic or peripheral procedure with or without the assistance of catheterization.

Additionally, another object of this invention is to provide methods, systems, and devices to enable the performance of minimally invasive anastomoses that do not require the interruption of blood flow in the receiving blood vessel.

Still another object of the present invention is to provide methods, systems, and devices that are versatile enough to be able to suitably combine a variety of cutting, welding, and joining techniques in the practice of vascular anastomosis.

A feature of the active endoscopic or peripheral procedure of this invention is that it can rely on catheter assistance that is provided following an intravascular approach. Accordingly, a catheter is inserted into and along the intraluminal space of a receiving blood vessel; characteristics of this catheter include its use for signaling the optimal anastomosis site at the time of performing an initial angiographic examination.

Another feature of the catheter assisted active endoscopic or peripheral procedure of this invention is that the minimally invasive anastomosis is performed with an extravascular endoscopic or peripheral device that is typically introduced percutaneously, and this is done in cooperation with endovascular vascular anvil and wire. The extravascular or device can be endoscopic or nonendoscopic. An extravascular endoscopic device is typically used in a procedure such as an intraabdominal or intrathoracic procedure, whereas a nonendoscopic extravascular device (hereinafter referred to as "peripheral device") is typically used when there is no need to use a visual aid, such as an endoscope, in a peripheral procedure.

One advantage of performing a minimally invasive anastomosis under the active endoscopic or peripheral procedure that is based on the methods, systems, and devices of the present invention is that its practice does not require the training in surgical methods and techniques that the practice of surgery requires. Cross-specialty teams of practitioners including those with training in endovascular intervention as well as conventional surgical training can consequently perform minimally invasive anastomoses according to the methods, apparatuses, and systems of this invention.

Another feature of the active endoscopic or peripheral procedure of this invention is that it directly employs information while it is being acquired in an angiographic examination. This efficient use of information, and in particular imaging, has the advantage that the anastomosis is actually performed in less time and without having to rely on the correlation of previously recorded images with external anatomic inspection for locating the optimal anastomosis site. The shorter procedure according to this invention consequently requires less or no hospitalization time and less medical resources.

Still another feature of the active endoscopic or peripheral procedure of this invention is that it requires no sutures. The avoidance of sutures has the advantages of reducing the invasive character of the procedure, reducing the number of mechanical elements in the practice of the anastomosis, and shortening the time needed to perform the anastomosis.

By not requiring the interruption of blood flow in the receiving blood vessel, the active endoscopic or peripheral procedure of this invention advantageously reduces or even eliminates the risk of ischemia in organs that receive their main supply of blood through the receiving blood vessel. Furthermore, the exposure of the anastomosis area is reduced because no devices have to be introduced to temporarily interrupt blood flow. This feature advantageously enhances the minimally invasive character of the methods, systems, and apparatuses of this invention and the intervention time for the practice of the anastomosis.

The minimal disruption of blood flow in the receiving blood vessel by the active endoscopic or peripheral procedure of this invention advantageously makes it suitable in the context of coronary artery bypass grafting (CABG), whether blood circulation is intracorporeal or extracorporeal, and whether the grafting is performed on a beating heart or an arrested heart.

Another feature of the active endoscopic or peripheral procedure of this invention is the efficient use of information and the simpler procedural and technical approach relative to more invasive procedures. This feature advantageously permits the reduction in the number of practitioners involved in the anastomosis and consequently enhances the consistency of the results, which become less operator-dependent.

The methods, systems, and devices of this invention enable the performance of minimally invasive vascular anastomosis following either a catheter assisted active endoscopic or peripheral procedure, or an active endoscopic or peripheral procedure in conjunction with a small incision at the anastomosis site. According to the first procedure, the anastomosis is preferably performed by inserting a catheter into and along the intraluminal space of a receiving blood vessel while an angiographic examination is taking place. The catheter distal end is intravascularly placed at the optimal anastomosis site and this site is signaled with the aid of one of the catheter's features. According to the second procedure, the vascular anvil and wire of this invention are introduced through a small incision performed at the receiving blood vessel's anastomosis site. This procedure is advantageous when catheterization is not desirable because of blood vessel damage or occlusion.

In one embodiment, the anastomosis site is signaled with a mechanical device such as a wire that has an anvil attached to it. The distal end of the wire is pushed along one of the catheter lumens so the wire's distal end pierces the wall of the receiving blood vessel from the intima outward through the media and adventitia. At the same time, a device such as an intravascular anvil that is attached to the wire abuts the wall of the receiving blood vessel at the anastomosis site, shaping the abutted portion of the wall at the site where the anastomosis fenestra will be opened. In another embodiment, the anastomosis site is also signaled with a mechanical device such a wire with an anvil attached to it. In this embodiment, however, the wire is inserted through a small incision on the receiving blood vessel at the anastomosis site. Piercing of the receiving blood vessel and abutting of its wall at the anastomosis site are subsequently performed according to a procedure that is analogous to that followed when the wire and anvil are introduced through a catheter.

An endoscopic or peripheral device preferably carries a compression plate device and the graft vessel, and engages the extravascular portion of the wire. This compression plate device includes two opposing and generally annular compression plates in a generally coaxial orientation. The end of the graft vessel that is to be anastomosed is everted and engaged with the aid of spikes to one of the compression plates of this invention. With the other compression plate placed at and around the anastomosis site, an anastomosis fenestra is opened in the wall of the receiving vessel. This anastomosis fenestra is opened within the annular region generally defined by the compression plate located at and around the anastomosis site. With the aid of the anvil of this invention, the contour of the anastomosed fenestra is engaged with the compression plate which opposes the compression plate that carries the graft vessel. This engagement is preferably accomplished with the aid of spikes protruding from the compression plate placed around the anastomosis fenestra. The graft vessel is subsequently approached to the anastomosis fenestra by reducing the separation between the compression plates, so that the spikes that hold the graft vessel to one of the compression plates cause the eversion of the contour of the anastomosis fenestra by appropriately sliding on the surface of the anvil. The relative separation of the compression plates of this invention is reduced to the extent necessary to bring the everted edges of the anastomosed structures into contact engagement so that a leak proof anastomosis is achieved.

A feature of the present invention is that the compression plate device is suitable for end-to-side anastomosis in addition to side-to-side anastomosis. Furthermore, the compression plate device of this invention provides support to the anastomosed structures in a manner such that the compression plates do not disrupt the periodic dilation of the anastomosed structures as is required by the characteristics of the blood flow that circulates therethrough. Moreover, the compression plate device of this invention is used, together with the anvil, to evert the contour of the anastomosed fenestra in the receiving vessel while the anastomosis takes place. In addition, the compression plate device of this invention can be used in conjunction with a vascular anvil and wire, regardless of whether the vascular anvil and wire are introduced into the receiving blood vessel with the aid of a catheter or directly into the intraluminal space through a small incision at the anastomosis site.

Another feature of the present invention is that the anvil is configured in a way such that it cooperates with the cutting element in the opening of the anastomosis fenestra and it also cooperates with the compression plate device in the eversion of the edge of the anastomosed fenestra. By joining the everted contour of the anastomosis fenestra with the everted edge of the graft vessel, significant exposure to the blood flow of the cut portion of the anastomosed structures is avoided. Furthermore, the use of the anvil of the present invention in a plurality of operations permits a considerable simplification of the anastomosis procedure. These operations include the abutting of the receiving blood vessel wall at the anastomosis site, the opening of the anastomosis fenestra in the receiving blood vessel, the eversion of edge of the anastomosis fenestra, and the joining of the anastomosed structures.

As discussed in more detail hereinbelow, the opening of the anastomosis fenestra can be performed mechanically or with the aid of a radiation-based device. The graft vessel is joined to the wall of the receiving blood vessel by a compression plate device. This device is configured in a manner such that it permits the use of supplementing joining techniques and combinations thereof. These techniques include welding, soldering, and gluing. Moreover, the signaling of the anastomosis site is preferably performed with the aid of a mechanical device such as the combination of a wire and an anvil.

A feature of the catheter assisted endoscopic or peripheral procedure of this invention is the versatility of the vascular anvil and wire for signaling the anastomosis site and of the extravascular device and cooperatively performing the anastomosis. Accordingly, a variety of devices and techniques can be advantageously combined in the context of this invention to enhance the performance of its methods, systems and devices.

These and other objects, features, and advantages of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIGS. 5A–5D are perspective views of four embodiments of the vascular anvil of this invention.

DETAILED DESCRIPTION OF THE PREFERRED EMBODIMENTS

The present invention focuses on catheter vascular anastomosis methods, systems and devices, and it relates to compression plate devices for anastomosis, to systems for carrying out anastomosis with such compression plates, and to anvils for performing such anastomosis. Embodiments of the compression plate devices according to this invention are configured so that they engage and hold together the anastomosed structures in an effective leak proof contact engagement. Embodiments of systems for carrying out anastomosis with such compression plates according to this invention include elements for intravascular access of and for opening an anastomosis fenestra at the chosen anastomosis site. Embodiments of compression plate devices and systems and embodiments of the vascular anvils of this invention are suited for the practice of catheter assisted anastomosis and also for the practice of anastomosis without catheterization.

Figure 6:
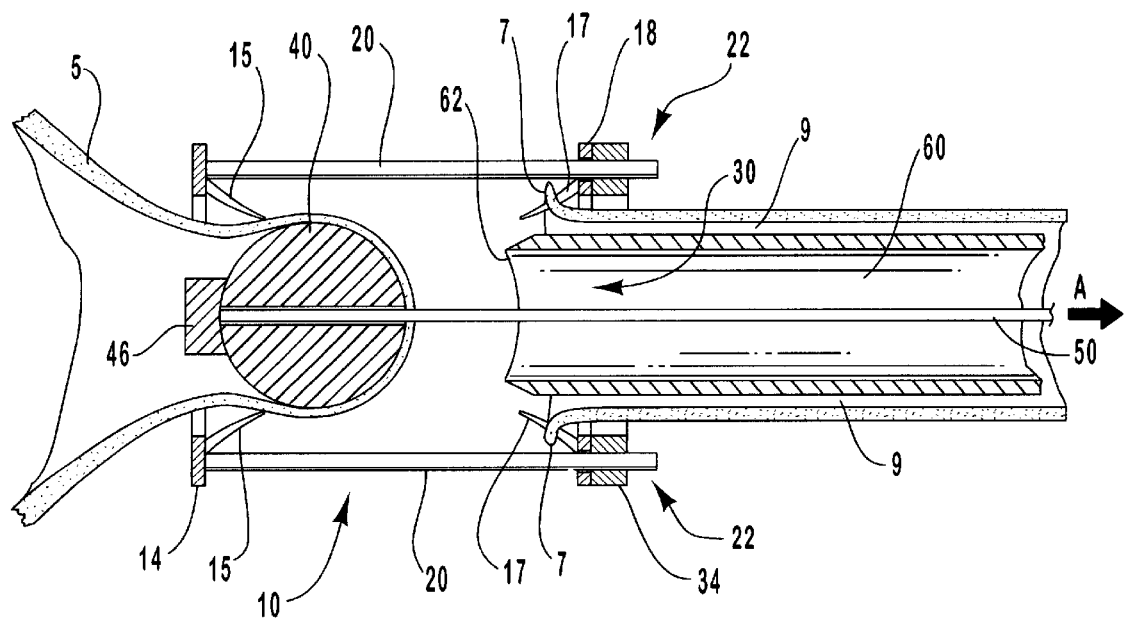
FIG. 6 shows a side, and partially cut away, view of an embodiment of a compression plate device in use with a cutter and graft vessel and with a wire and vascular anvil system as configured at an early stage of an end-to-side anastomosis.
Figure 7:
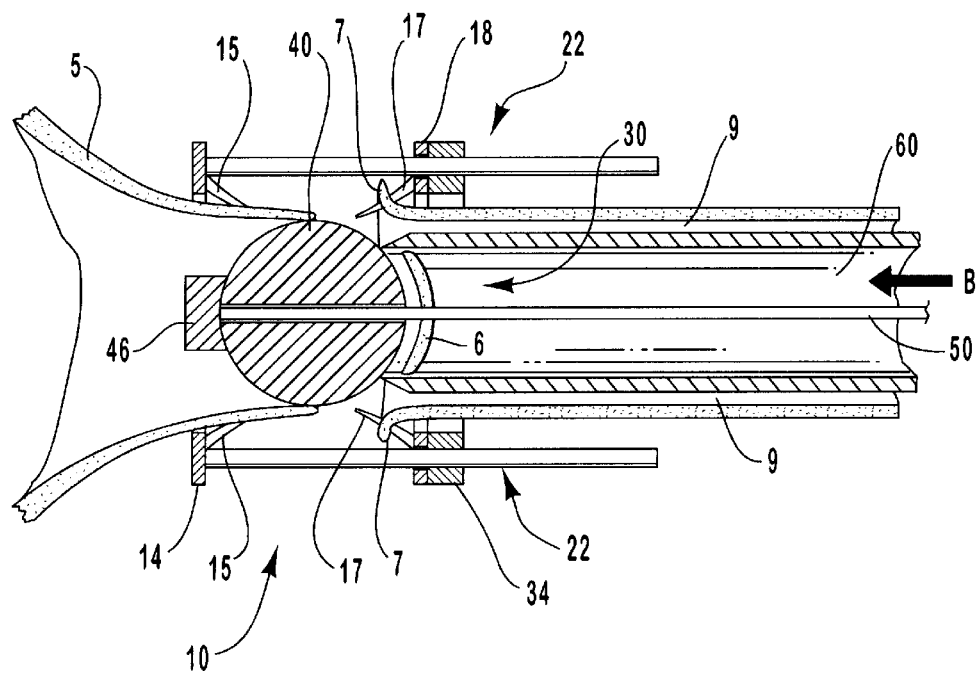
FIG. 7 shows the embodiments displayed in FIG. 6 as configured at a later stage in the practice of an anastomosis.
Figure 8:
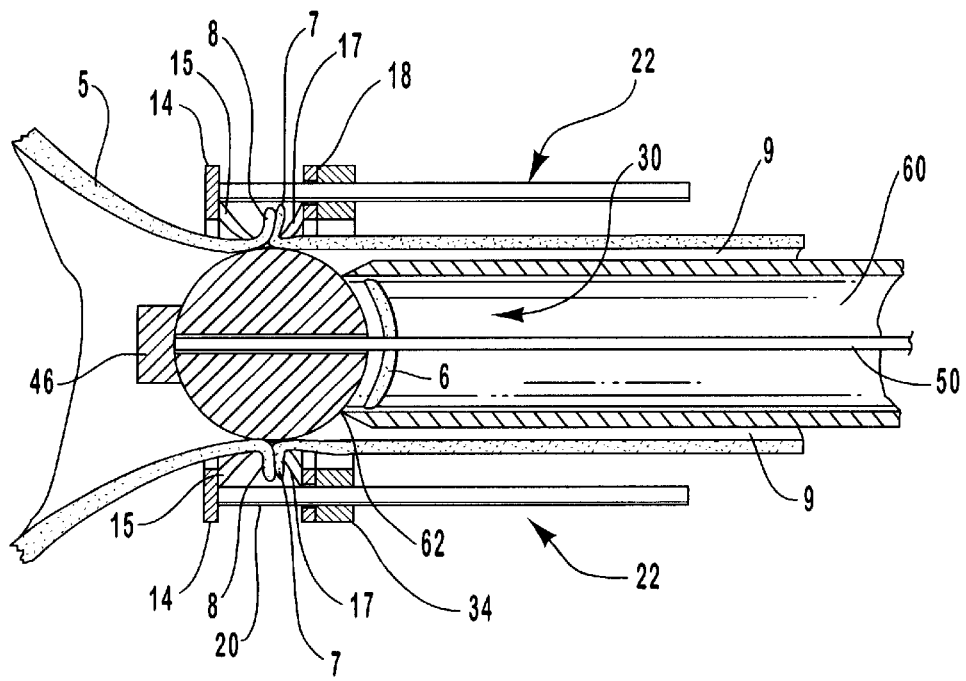
FIG. 8 shows the embodiments displayed in FIG. 7 as configured at a later stage in the practice of an anastomosis.

Embodiments of compression plate devices according to this invention are schematically illustrated in FIGS. 2B, 3 and 6–9. FIGS. 4 and 6–9 schematically illustrate different relative configurations of an embodiment of a compression plate device and other elements of an embodiment of a compression plate system for carrying out anastomosis according to this invention. FIG. 8 schematically illustrates two structures that are anastomosed in an end-to-side anastomosis with an embodiment of a compression plate device according to this invention.

The anastomosed structures are maintained together according to this invention so that they are effectively anastomosed in a leak proof manner. In one embodiment of this invention, this is accomplished with a compression plate device such as compression plate device 10 shown in FIG. 1. In other embodiments, this is accomplished by a compression plate device such as compression plate device 11 shown in FIG. 2B. FIG. 3 also shows compression plate device 11 in conjunction with other elements such as a cutter and an anvil.

In this embodiment, plates 14 and 18 are configured so that they provide support to the everted openings of the anastomosed structures. Plates 14 and 18 are provided with respective openings 32 and 30. Plates 14 and 18 are generally annular with preferably circumferential outer edges, although ellipsoidal, ovoid, or edges with generally curvilinear shapes are also envisaged as edges of other embodiments of this invention.

Compression Plates

In each compression plate, the side which is in contact with the everted contour of the anastomosed structure is described as the anastomosis side. In the practice of an anastomosis according to this invention, compression plates are used in a way such that the anastomosis sides of the two compression plates are opposite to each other. Preferred embodiments of compression plates have a generally annular shape with interior openings which have a generally circumferential contour; the internal diameter of each one of these openings is such that the corresponding portion of the vessel to be anastomosed can fit therein. Typically, this internal diameter is approximately equal to, or slightly greater than, the external diameters of the corresponding portion of the vessel to be anastomosed. An internal diameter slightly greater than the external diameter of the corresponding portion of the vessel to be anastomosed is preferred. With this internal diameter, the compression plate does not pose a significant obstacle to the periodic dilation that the vessel is subject to as a consequence of the characteristics of the fluid flow that circulates through the anastomosed structures.

Compression plates 14 and 18 are also configured so that they can effectively engage the structures to be anastomosed and thus effectively hold such structures. Compression plates 14 and 18 are configured so that the holding of the anastomosed structures is achieved at least in one of the following ways. Holding by contact engagement, holding by penetration, and holding by binding. The description below of the additional features of the exemplary embodiments of compression plate devices will illustrate these different types of holding by compression plates 14 and 18.

Figure 1:
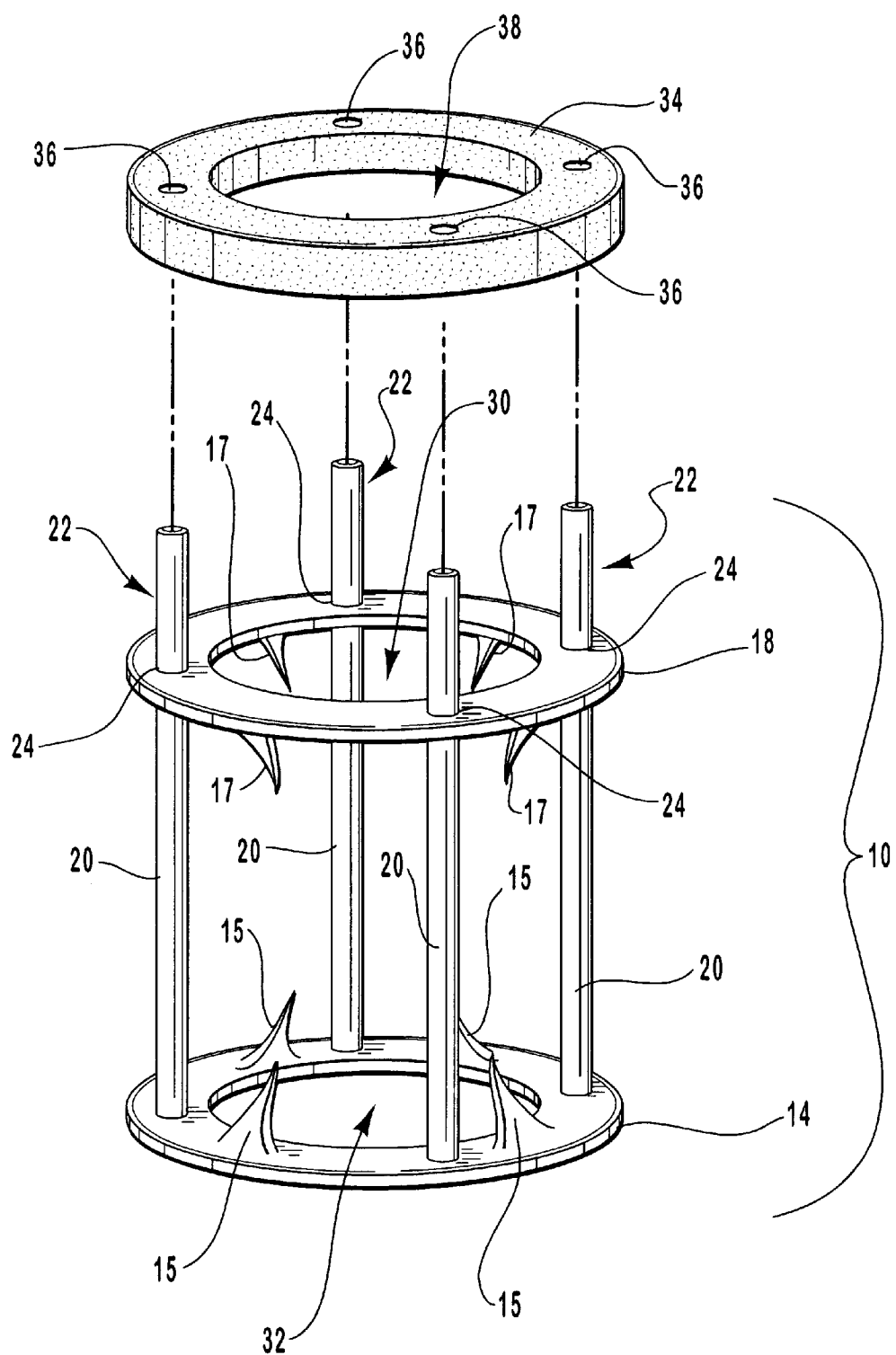
FIG. 1 shows a partially exploded perspective view of an embodiment of a compression plate device for anastomosis according to this invention.

Compression plates 14 and 18 are provided in the exemplary embodiment shown in FIG. 1 with spikes 15 and 17 respectively protruding from opposing anastomosis sides of compression plates 14 and 18. Spikes 15 and 17 are intended to penetrate or even puncture and hold the everted contours of the structures being anastomosed. Each one of spikes 15 and 17 has a base that is integrally attached to the anastomosis side of the corresponding plate and a sharp tip opposed to such base. Spikes 15 and 17 are manufactured and disposed so that they can elastically bend in such a way that the tips of such spikes slightly swing about their respective bases. Once the bending action has ceased, spikes 15 and 17 elastically move towards their initial configurations. This bending action can be caused by the displacement through any of openings 32 and 38 of an object with a curved surface moving past the spike bases towards the spike tips. This bending action can also be accomplished by pushing the spike tips against a surface which has the appropriate curvature.

When holding by penetration relies on spikes such as spikes 15 and 17, at least one spike is provided in the anastomosis side of each plate. A number of spikes ranging form six to ten is preferred, although some embodiments of this invention are envisaged with less than six or more than ten spikes. The exemplary embodiment shown in FIG. 1 displays four spikes integrally attached to the anastomosis side of compression plate 14 and four spikes integrally attached to the anastomosis side of compression plate 18.

Spikes such as spikes 15 and 17 can have a plurality of shapes. The spikes preferably used in embodiments of this invention are wider at the base and so configured as to extend into a terminal puncturing tip at the end opposite to the base. Although spikes 15 and 17 can be distributed in a variety of arrays, a generally regular distribution on the anastomosis sides of the compression plates is preferred. Most embodiments of the compression plates of this invention contain a number of spikes between six and ten. For example, the embodiment shown in FIGS. 2A–2B has eight spikes in each compression plate.

Each of the spikes shown in the embodiment schematically depicted in FIG. 1 is attached at its base to the anastomosis side of a compression plate. The attachment sites are located in this embodiment between the inner and the outer perimeter of each annular compression plate.

Figure 2A:
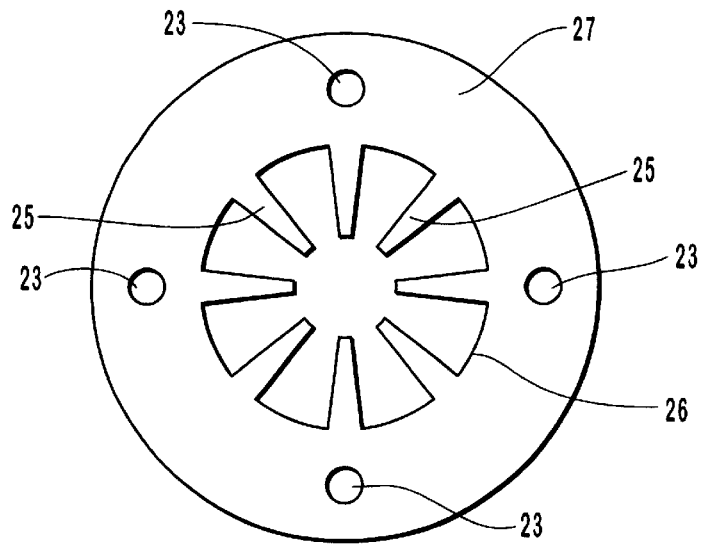
FIG. 2A shows a top view of an embodiment of a compression plate with eight spikes disposed around the inner periphery of an annular plate.

The spikes can be attached at other sites, however, as shown in the embodiment depicted in FIG. 2A. The top view of this embodiment shows eight spikes 25 disposed around inner periphery 26 of annular compression plate 27. A variety of techniques known in the art can be used to manufacture compression plates within the scope of this invention. One technique comprises the cutting of the interior of a disc according to the pattern shown in FIG. 2A and the subsequent bending of the spikes at their bases. This bending preferably takes place prior to the use of the compression plates in the anastomosis procedure. However, bending of the flat spikes during the anastomosis procedure is envisaged in other embodiments of this invention.

Spikes of a variety of shapes which are distributed in varying numbers and arrays on the anastomosis sides of compression plates 14 and 18 and equivalents thereof are exemplary embodiments of means for holding anastomosed structures.

Compression plates 14 and 18 are configured in such a manner that they can be approached or separated relative to each other so that spikes 15 and 17 are maintained in a relative opposing orientation. This configuration can be achieved, for example, with one of these plates, which in the embodiment shown in FIG. 1 is compression plate 18, slidably mounted on guides 20 at sliding sites 24. To slide compression plate 18 along guides 20, each one of ends 22 of guides 20 is introduced through one of sliding sites 24 of compression plate 18. Ends of guides 20 opposite to ends 22 are attached in the embodiment shown in FIG. 1 to the anastomosis side of compression plate 14.

Embodiments of compression plate anastomosis devices according to this invention are provided with at least one holding element. As shown in FIG. 1, a preferred embodiment of this holding element is a holding ring 34 that has a friction coupling with guides 20 at orifices 36. Holding ring 34 is provided with window 38 whose internal diameter is preferably at least equal to that of the opening 30 of compression plate 18. The friction coupling of holding ring 34 with guides 20 is such that expansion of the anastomosed structures can not separate compression plates 18 and 14 with respect to each other when holding ring 34 is in contact engagement with the side of compression plate 18 opposite to its anastomosis side. Other embodiments of this invention are provided with different holding elements that are designed to prevent compression plate 18 from significantly moving away from compression plate 14. This separation could be caused, for example, by an expansion of the anastomosed structures at the anastomosis site, caused in turn by the pressure exerted by the fluid circulating therethrough. Examples of these additional embodiments include individual friction coupling rings designed to fit each individual guide 20, and holding rings or individual rings provided with features that are configured for mating engagement with notches or other features formed in guides 20.

The compression plates of this invention can be approached to a desired relative separation and maintained at that separation with the aid of a holding element. This feature permits the control of the pressure applied to the everted tissue of the anastomosed structures. This pressure control allows in turn to perform the anastomosis in the most suitable manner depending on variables such as the pressure of the fluid that circulates through the anastomosed structures and the nature of the everted tissue at the anastomosis site.

A number of embodiments of compression plate anastomosis devices according to this invention are provided with at least one guide 20, and preferably with a number of guides between three and six. The exemplary embodiment shown in FIG. 1 is provided with four guides 20, but other embodiments of this invention can have less than three or more than six guides. Although guides 20 can be distributed in a variety of arrays, a generally regular distribution is preferred in embodiments with more than one guide.

When compression plates 14 and 18 are in close proximity to each other at an anastomosis site providing support to the anastomosed structures, terminal ends 22 of guides 20 can extend away from compression plates 14 and 18 to an extent such that the protrusion results in the presence of an undesirable feature in the immediate neighborhood of the anastomosis site. To solve this problem, embodiments of the compression plate devices of this invention are provided with guides 20 which can be appropriately shortened by removing an appropriate length of terminal ends 22. In some embodiments, terminal ends 22 are manufactured with a material which dissolves after an appropriate time following the anastomosis. In other embodiments, guides 20 are made of a material that can easily be clipped to a desired length, thus eliminating terminal ends 22. In other embodiments, guides 20 can be provided with notches or some other localized weakened structural feature which facilitates the easy removal of terminal ends 22 at desired distances with respect to plate 14. Still other embodiments can be provided with terminal ends 22 that can easily bend to an extent such that undesirable protrusions are eliminated.

Guides of a variety of lengths, which are distributed in varying numbers and arrays, and which are manufactured in any one of a variety of manners that permit their appropriate shortening if necessary, and equivalents thereof, are exemplary embodiments of means for guiding the movement of one compression plate with respect to the other compression plate.

Although guides such as guides 20 provide a convenient structural element for appropriately orienting and approaching the compression plates of this invention relative to each other, the appropriate orientation and relative displacement of the compression plates can be achieved in other ways that accomplish the same effects. These different ways of providing the appropriate relative orientation of the compression plates and the relative displacement are within the scope of this invention. For example, a device used to insert the compression plates or to insert the cutting element that is needed to open the anastomosis fenestra can provide the appropriate support for orienting and displacing the compression plates relative to each other. In this case, an embodiment of the compression plates of this invention is schematically depicted in FIG. 2B.

The spikes in each compression plate of this invention are preferably oriented relative to the spikes in the other compression plate in a mating configuration. When referring to the relative configuration of the spikes in opposing compression plates, the terms "mating configuration" describe a configuration in which each one of the spikes in a compression plate can generally fit in the space between two neighboring spikes in the opposing compression plate when such compression plates are close enough. This relative orientation is illustrated in the embodiment shown in FIG. 2B by the dashed lines drawn therein. As indicated above, structural elements such as guides 20 are used in some embodiments of this invention to orient the compression plates so that the respective teeth have the preferred mating configuration.

Figure 2B:
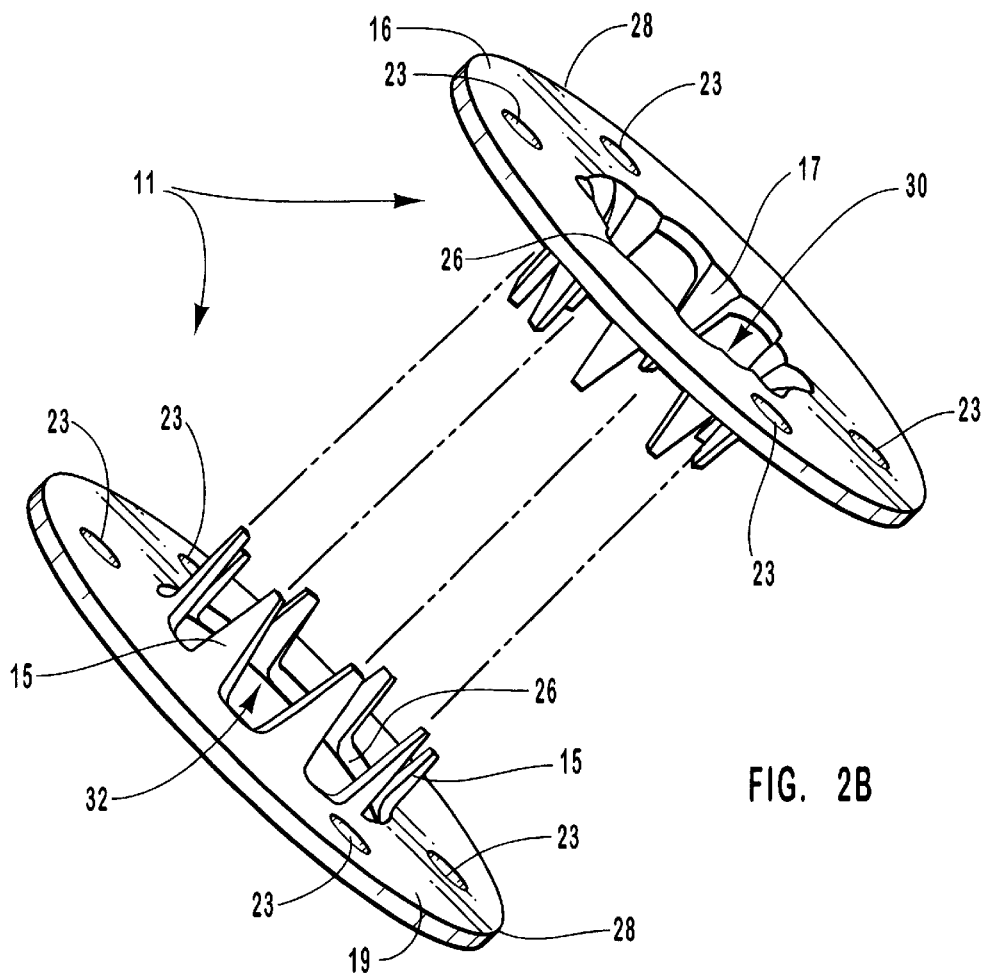
FIG. 2B shows a perspective view of two compression plates at a relative orientation such that the respective teeth are in a mating arrangement.
Figure 3:
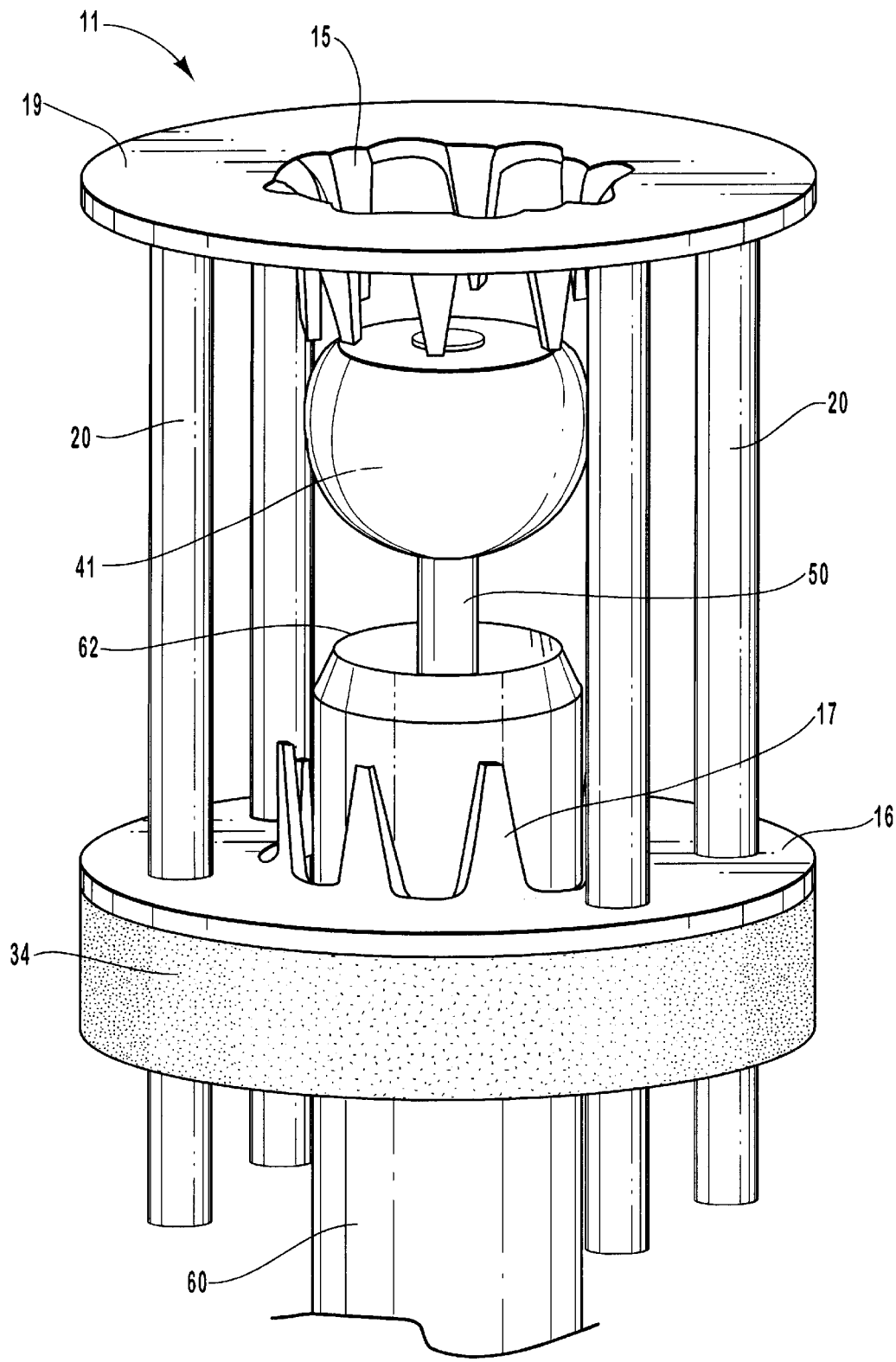
FIG. 3 shows a perspective view of an embodiment of the compression plate anastomosis device with additional elements such as an anvil and a cutter.

FIG. 2B shows another embodiment 11 of compression plates of this invention. Spikes 15 and 17 are disposed in this embodiment along inner periphery 26 of the generally annular compression plates 19 and 16. With the spikes disposed in this preferred location, the compression plates of this invention can provide appropriate support to the anastomosed structures without significantly obstructing the periodic dilation to which the anastomosed structures are subjected as a consequence of the characteristics of the fluid flow that circulates therethrough.

Embodiments of spikes of this invention, such as spikes shown in FIGS. 1 and 2B, are preferably configured in a way such that they are not exposed to blood flowing through the anastomosed structures. Some embodiments of this invention are provided with spikes that are coated with a biocompatible non-thrombogenic material to prevent the formation of thrombi if such spikes or any portion thereof were exposed to blood flow. This coating material should not impede the penetrating ability of the spikes. An example of such material is teflon.

Aligning elements 23 in the embodiment shown in FIG. 2B represent sliding sites like sliding sites 24 shown in FIG. 1 or any other feature that can be used for orienting compression plates 16 and 19 relative to each other. For example, aligning elements 23 can be receiving or protruding features that are designed to engage mating features in an aligning device. Appropriate relative orientation of compression plates 16 and 19 can also be achieved with the aid of notches or other aligning features in the outer peripheries of compression plates 16 and 19.

As shown in FIGS. 1, 2B, and 3, the anastomosis side of each one of the compression plates of this invention is the side of the anastomosis plate towards which the spikes are bent. The anastomosis side of a compression plate is also referred to as the side of the compression plate to which spikes are attached, whether the spikes are attached somewhere between the inner and outer peripheries of a compression plate or they are attached along the inner periphery of a compression plate.

Embodiments of compression plates such as compression plate 14 in FIG. 1 and compression plate 19 in FIG. 3 remain at the anastomosis site nearer to the receiving blood vessel than embodiments of compression plates such as compression plate 18 in FIG. 1 and compression plate 16 in FIG. 3. Accordingly, embodiments of compression plates such as compression plates 14 and 19 are described as receiving vessel side compression plates. Embodiments of compression plates such as compression plate 18 in FIG. 1 and compression plate 16 in FIG. 3 hold the graft vessel, and they are according described as graft side compression plates.

FIG. 3 schematically shows a perspective view of an embodiment 11 of a compression plate anastomosis device with anvil 41 and wire 50 according to this invention. Compression plates 16 and 19 in this embodiment are provided with teeth 17 and 15, respectively similar to the teeth of the embodiment shown in FIG. 2B. Four guides 20 in the embodiment shown in FIG. 3 embody the orienting element for compression plates 16 and 19. In addition, guides 20 permit the relative approach of these two plates. This approach is achieved in the embodiment shown in FIG. 3 by sliding compression plate 16 along guides 20 towards compression plate 19.

FIG. 3 shows wire 50 extending within and along cutter 60 from anvil 41 which is braced against wire 50. In this configuration, a cutting action by cutting edge 62 can be achieved in several ways. For example, such cutting action can be achieved by pulling wire 50 so that the convex surface of anvil 41 is driven towards and against cutting edge 62. Another operation that will also lead to a cutting action comprises pushing cutter 60 towards and against the convex surface of anvil 41 while wire 50 is held so that the convex surface of anvil 41 becomes the receiving surface of an effective cutting action by cutting edge 62. In addition, a cutting action can be achieved by effectively combining the two operations previously described. Any one of these cutting actions will cut a section along cutting edge 62 of a material disposed on at least a portion of the convex surface of anvil 41 around wire 50. For example, any one of this cutting actions will cut a generally circular portion of a blood vessel wall that is disposed around wire 50 and on the convex surface of anvil 41.

FIGS. 1 and 3 depict an embodiment of an optional holding element according to this invention which is embodied as holding ring 34. For example, this holding element can be a nylon plastic friction coupler that slides along guides 20 towards compression plate 19, but that offers sufficient friction resistance to keep compression plates 16 and 19 at approximately constant relative separation when a structure sandwiched between compression plates 16 and 19 tends to expand. In the absence of a suitable holding element, this expansion would push compression plate 16 away from compression plate 19, and the leak-proof character of structures held together by compression plates 16 and 19 could thus be lost.

Spikes in embodiments of this invention, such as the spikes shown in FIGS. 1, 2B, and 3, are preferably configured in a way such that their tips are slightly pushed by the anvil when the anvil is advanced through the compression plate's opening towards the opposing compression plate. After the tips of the spikes are so pushed by the advancing anvil, the curvature of the anvil is such that it permits the tips of the spikes to elastically relax towards their initial configuration.

The structures to be anastomosed are inserted in an embodiment of this invention, such as any of the embodiments schematically shown in FIGS. 1, 2B, and 3 through openings 30 and 32. For example, the anastomosis end of the graft vessel is inserted through opening 30 and it is so disposed that its everted end is held by spikes 17.

The anastomosis fenestra in the receiving vessel is opened according to this invention with a vascular anvil and wire, such as anvil 40 and wire 50 schematically shown in FIGS. 3 and 4 and whose use is described hereinbelow.

Vascular Anvil and Wire

Some embodiments of this invention utilize a catheter with its distal end so configured that it directs the sharp distal end of a wire towards the intima of a blood vessel. The wire's distal end that is so directed punctures the wall of the blood vessel creating a passage from the intraluminal to the extraluminal space of the blood vessel wall through which the wire can extend as it is being inserted within and along the catheter. This intraluminally directed procedure and devices to implement it have been described in co-pending U.S. patent application Ser. No. 09/293,366 for Methods, Systems and Apparatus for Intraluminally Directed Vascular Anastomosis, and 09/293,617 for Anastomosis Apparatus for Use in Intraluminally Directed Vascular Anastomosis, both claimed by Dr. Duane D. Blatter, which are incorporated herein by reference in their entirety for the purpose of this description.

Figure 4:
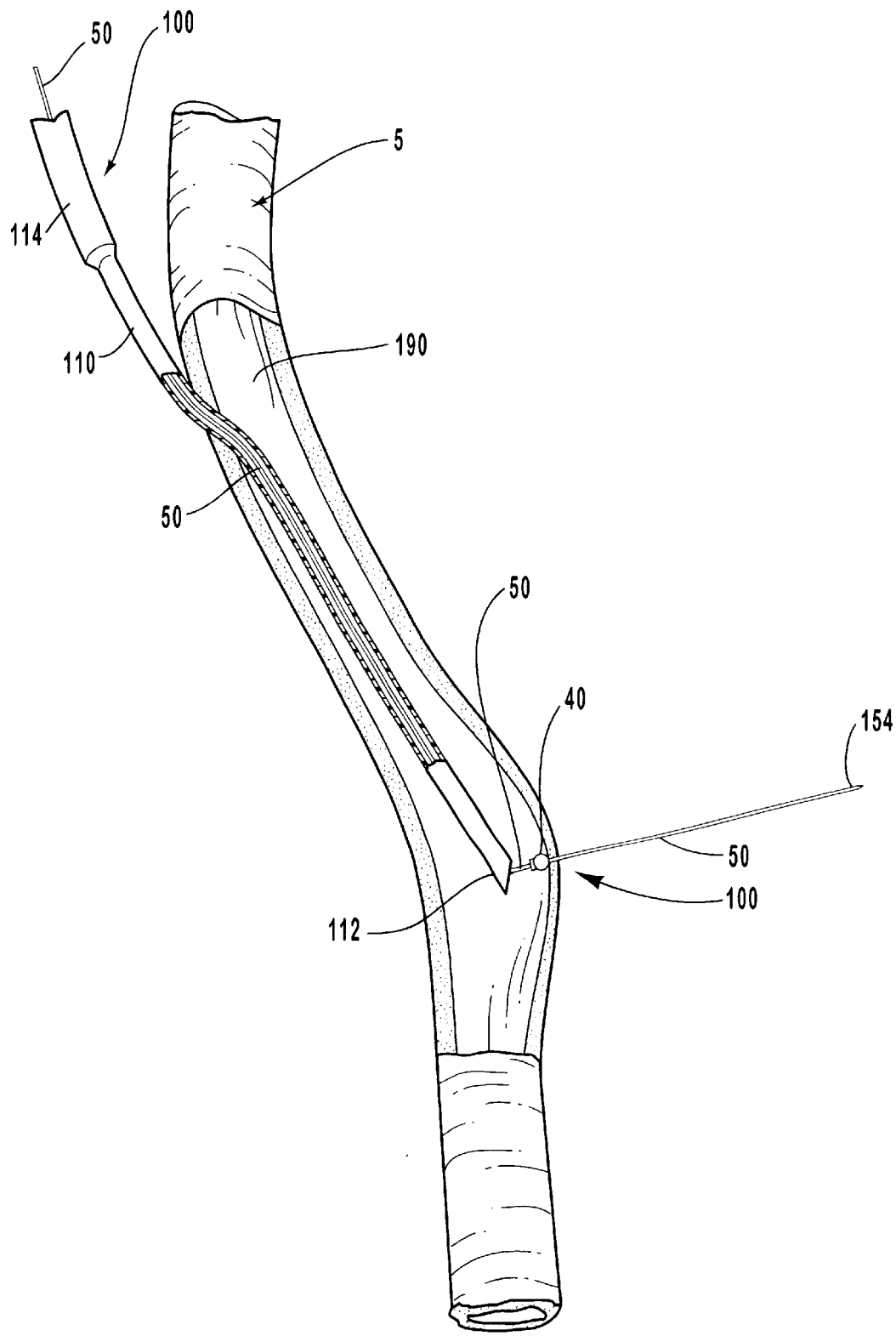
FIG. 4 is a partially cut-away view of a general disposition of an intraluminally directed anvil and wire.

As schematically shown in FIG. 4, the anastomosis site is signaled according to this invention with the aid of an imaging technique and an intraluminally directed vascular anvil that is embodied in FIG. 4 by catheter apparatus 100. Catheter apparatus 100 comprises tubular shaft 110, wire 50, and anvil 40. This embodiment of an intraluminally directed apparatus is referred to as a catheter apparatus.

Distal end 112 of tubular shaft 110 can be percutaneously introduced in the intraluminal space 190 of receiving blood vessel 5 according to conventional catheterization techniques. For example, dilatators are used as known in the art, and the catheter dimensions are suitably chosen depending on the distance from the catheterization site to the anastomosis site and depending on the size of the anvil to be inserted. In some of the experiments performed in the context of this invention, a catheter characterized as a 13 French sheath, also known as a 4.3 mm catheter—1 French unit=⅓ mm—, has been found suitable for most vascular anvil and wire insertions. Catheterization techniques are described, for example, by Constantin Cope and Stanley Baum, Catheters, Methods, and Injectors for Superselective Catheterization, in Abrams' Angiography, edited by Stanley Baum, 4th ed., (this work will hereinafter be referred to as "Catheters, Methods, and Injectors") which is hereby incorporated by reference in its entirety.

Tubular shaft 110 is inserted along intraluminal space 190 until distal end 112 reaches the proximity of a blood vessel occlusion or another abnormality that has been detected by a conventional exploration technique. With tubular shaft 110 so disposed, piercing wire 150 is introduced into tubular shaft 110 through proximal end 114 so that it extends along tubular shaft 110. Wire 50 is inserted within and along tubular shaft 110 of catheter apparatus 100 so that distal piercing end 154 punctures receiving blood vessel 5 from its intraluminal space and it extends outwardly by protruding at the chosen anastomosis site. To facilitate this operation, distal end 154 is preferably sharp enough as to be able to puncture the wall of receiving blood vessel 5 from its intima outwards without causing undue tearing around the puncture.

Wire in the context of this invention refers to any thin and elongated device with a distal end configured for penetrating the wall of a blood vessel. A guide wire suited for inserting both diagnostic and therapeutic catheters is disclosed in U.S. Pat. No. 4,846,186, which is hereby incorporated by reference in its entirety, and catheters and guide wires for vascular and interventional radiology are disclosed in Catheters, Methods, and Injectors, at 155–174, which is also hereby incorporated by reference in its entirety. Wire 50, however, is preferably pointed and sharp to effectively puncture the wall of receiving blood vessel 5.

Wire 50 in the embodiment shown in FIG. 4 extends from anvil 40 towards the anastomosis site and towards the catheter insertion site. In other embodiments, wire 50 is pulled from outside vessel 5 once it has punctured its wall until the end of wire 50 opposite to the puncturing end engages anvil 40. A stopping element, such as stopping element 46, can be used to brace anvil 40 to the end of wire 50 that is opposite to the same wire's piercing end 154. In other embodiments of this invention, the anvil is attached to the wire. The length of wire 50 varies depending on the separation between the insertion site of catheter apparatus 100 and the anastomosis site. For example, this length would be approximately 180 cm long, depending on the patient's height, if an anastomosis were to be performed in a blood vessel in the arm such as the brachial artery, and catheter apparatus 100 were inserted into the femoral artery.

Distal end 112 can be modified to provide a lateral exit to distal end 154 of wire 50. Distal end 112 in one embodiment comprises a deflecting surface and a lateral aperture that guides piercing end 154 of wire 50 towards the intima of receiving blood vessel 5. Because piercing end 154 is very sharp, such deflecting surface is preferably a puncture and abrasion resistant surface. In addition, distal end 112 can be provided with an appropriate marker for imaging the orientation of the aperture at distal end 112 and/or the position of distal end 112 itself. Such radio-opaque markers can be any of the radio-opaque markers known in the practice of angiography. Wire 50 is typically radio-opaque itself, although very thin embodiments of this wire are preferably coated with a material such as gold or a bio-compatible barium-containing substance to make them more visible. Catheter distal end configurations for directing outwardly an elongated member have been disclosed in U.S. Pat. Nos. 4,578,061, 4,861,336, 5,167,645, 5,342,394, and 5,800,450, which are hereby incorporated by reference in their entirety.

In one embodiment, the intraluminally directed anvil apparatus, such as catheter apparatus 100, comprises an anvil that is introduced in intraluminal space 190. The anvil of this invention provides a receiving surface to be in direct contact with the blood vessel's intima at the anastomosis site when the anvil abuts the receiving blood vessel wall. Anvil 40 is sized so that it can slide within the lumen of tubular shaft 110 while presenting a surface which has an area approximately matched to the cross-sectional area of the lumen of the graft vessel to be anastomosed. Anvil 40 is preferably made of a puncture resistant material that can withstand the abrasive action of a cutting element. For example, anvil 40 is preferably made of stainless steel when it is to withstand the abrasive action of a cutting device or of a sharp pointed end. When cutting the anastomosis fenestra with radiant energy, the anvil of this invention is preferably coated with radiation absorbing material that prevents radiation scattering. Such coated anvil embodiments are hereinafter referred to as "laser shield anvils".

The dimensions of any of the embodiments of the anvil of this invention are determined by the size of the lumen of the receiving vessel and by the dimension of the passage that will ensure the fluid communication between the graft vessel and the receiving vessel after they have been anastomosed. These dimensions are typically chosen or known in the art. For example, when a graft vessel of about 4 mm in diameter is to be anastomosed to a receiving blood vessel which has an approximate lumen diameter of about 8 mm, the diameter of a generally spherical anvil according to this invention would range from about 3 mm to about 4.5 mm. The compression plate anastomosis device of this invention is preferably used for vascular anastomosis of vessels with diameters ranging from about 2 mm to about 20 mm, but there is no fundamental limitation for using embodiments of this invention with graft vessels whose diameter is less than 2 mm.

In general, the material of which any of the exemplary embodiments of the anvil of this invention is made is appropriately chosen to be abrasion resistant and/or an effective absorber of radiation depending on whether it is to be exposed to the abrasive action of a cutting device or to radiation. A cutting device can be, for example, a cutting edge, and radiation can be emitted by, for example, a surgical laser.

It is understood that the shapes, specific geometric features and constitutive materials of the foregoing embodiments of catheter apparatus 100 are given for exemplary purposes and they and/or equivalents thereof can be suitably combined or varied by one of ordinary skill in the art to satisfy the objectives of this invention.

The proximal end of the intraluminally directed apparatus of this invention, and in particular proximal end 114 of catheter apparatus 100, can comprise one or a plurality of access ports or luer fittings. For the purpose of simplicity, only one access port is shown in the embodiment of catheter apparatus 100 schematically shown in FIG. 4. Also for the purpose of showing a simple sketch, the embodiment of catheter apparatus 100, as schematically shown in FIG. 4, only displays one lumen, but catheter apparatus 100, and more generally the intraluminally directed anvil apparatus, can also have a plurality of lumens. The manufacture and handling of an apparatus with a plurality of lumens and a plurality of access ports are part of the ordinary skill in the art. For example, U.S. Pat. Nos. 5,662,580 and 5,616,114, which have herein been incorporated by reference in their entirety, disclose catheters with a plurality of access ports or luer fittings and a plurality of lumens.

Intraluminal access to the anastomosis site in the receiving blood vessel can be impeded by an occlusion or by blood vessel damage. In this case, a catheter cannot be used to intraluminally access the anastomosis site. Instead, other embodiments of this invention rely on the intraluminal access to the anastomosis site through a small incision, such as an arteriotomy, made at the anastomosis site. The wire and anvil are inserted through such incision and the abutting of the receiving blood vessel from its intraluminal space is then performed in the same way as when the anvil and wire are inserted with the aid of a catheter.

Embodiments of the anvil of this invention can be designed so that the blood flow through the receiving blood vessel will preferably not be interrupted during the anastomosis. However, the design can be such that the blood flow is interrupted when this feature is desired. The term "anvil" in the context of this invention is used herein as a short form for "vascular anvil" and it is meant to encompass objects with the characteristics described hereinabove which present at least one curved surface and which are configured in a manner such that they can interact with the compression plate device of this invention as described hereinbelow.

FIGS. 5A–5D show as examples several embodiments of the anvil of this invention. FIG. 5A schematically shows a generally spherical anvil 42 with portion of wire 50 which is slidably mounted through anvil 42. FIG. 5B schematically shows anvil 41 in which a polar cap has been replaced by surface 45. This surface is flat in some embodiments of the anvil of this invention whereas it is in other embodiments a convex surface whose curvature is different from that of the rest, generally spherical, anvil 41. FIG. 5C schematically shows anvil 43 that is generally similar to the anvil shown in FIG. 5B. In this embodiment, chamfered portion 47 is configured so that the sliding of a spike tip from surface 45 towards the generally spherical body of anvil 43 is facilitated. FIG. 5D schematically shows anvil 44 with a more pronounced curvature in one of the anvil's polar regions.

Stopping element 46 in FIGS. 5A–5D prevents wire 50 from passing completely through anvil 50. It is understood that stopping element 46 can be embodied by any other equivalent feature that engages the anvil of this invention and performs the functions described herein. With the functional specifications provided herein, the design of such equivalent features merely requires common skill in the art. Stopping element 46 is designed in a way such that when wire 50 is pulled, the effect of such pulling action is effectively communicated to the anvil by stopping element 46 abutting against the anvil. Alternatively, another embodiment of the anvil of this invention is bonded and fixed to the wire. With stopping element 46 in this abutting configuration, the anvil of this invention is configured to withstand a pressure exerted at the generally opposite side of the anvil. In the practice of an anastomosis according to this invention this pressure is due to the resistance exerted by the receiving blood vessel wall being distended by the anvil. When the cutting element that is used to open the anastomosis fenestra of this invention is embodied by a cutter with a cutting edge, the anvil of this invention also withstands the pressure exerted against it by the cutting edge of the cutter.

Line 48 in the embodiments of the anvil of this invention, such as the embodiments shown in FIGS. 5A–5D, is a visual aid to indicate a reference region of the different embodiments of the anvil. This region corresponds to a surface area around the perimeter of the anvil on which the leak proof engagement of the anastomosed structures according to the present invention is effectuated. In embodiments of this invention with compression plates that are provided with mating spikes, this region also corresponds to the general surface area around the perimeter of the anvil where the mating of the spikes preferably takes place. More specifically, spikes attached to a compression plate are configured to slide on a portion of the anvil surface on one side of line 48 and move towards the region indicated by line 48. Spikes attached to the opposing compression plate are configured to slide on a portion of the anvil surface on the other side of line 48 and move also towards the region indicated by line 48. Mating of the spikes attached to opposing compression plates is preferably achieved in a region at or near line 48. As indicated above, examples of spikes and compression plates of this invention are provided by the embodiments schematically shown in FIGS. 1, 2A–2B, and 3.

Other embodiments (not shown) of anvils of this invention include anvils with curved surface features that are designed to perform functions equivalent to those described herein for the examples schematically shown in FIGS. 5A–5D. These additional embodiments can be designed by combining features of the embodiments shown in FIGS. 5A–5D. Additional embodiments can also be designed by replacing geometric features of the anvils schematically shown in FIGS. 5A–5D by features that would perform the functions described herein. These combinations and replacements, however, can be performed by using ordinary skills in the art and the teachings provided herein, and such additional embodiments are consequently not explicitly illustrated herein with additional figures.

The anvil of this invention is configured in a way such that it effectively cooperates with the cutting element in the opening of the anastomosis fenestra and it also cooperates with the compression plate device in the eversion of the edge of the anastomosed fenestra. Furthermore, the anvil of the present invention is configured so that it can abut the receiving blood vessel wall at the anastomosis site from the intraluminal space of such blood vessel. In addition, the anvil of this invention is configured so that it effectively cooperates with the compression plates in the joining of the anastomosed structures. The functional implications of these features of embodiments of the anvil of the present invention will become more apparent in the discussion of FIGS. 6–9 provided below.

A variety of techniques can be used to introduce any of the herein disclosed exemplary embodiments of the anvil of this invention, including also any of their equivalent embodiments, into the receiving blood vessel and subsequently position it at the anastomosis site. As indicated above, a catheter is introduced in some embodiments into the receiving blood vessel with the aid of a guide wire, which is removed once the catheter is properly positioned. It is within and along this catheter that a piercing wire with an anvil attached thereto, as shown in the embodiment depicted in FIG. 4, is introduced and placed at the anastomosis site. With the anvil so positioned at the anastomosis site, the receiving blood vessel is then pierced with the piercing wire. Piercing end 154 of wire 50 is then pulled from the outside of receiving blood vessel 5 and inserted through the compression plates as shown in FIG. 6. In other embodiments, an embodiment of an anvil is placed intraluminally with a wire at the anastomosis site through a small incision made into the receiving blood vessel.

Anastomosis With A Compression Plate Device

FIG. 6 schematically shows a system of compression plates 10 in an appropriate configuration for initiating a side-to-end anastomosis. Although the numerals that label the features of the compression plates in FIGS. 6–9 are the same as the numerals used in the embodiment shown in FIG. 1, the embodiments shown in FIGS. 2A–2B and 3, and equivalents thereof, can also be used according to this invention as illustrated by the embodiments shown in FIGS. 6–9 and their corresponding descriptions provided hereinbelow. Similarly, the anvil shown in FIGS. 6–9 can be embodied by any of the anvils shown in FIGS. 5A–5D and by any of the equivalents thereof.

Wire 50 is intraluminally inserted into and along receiving blood vessel 5 so that puncturing end (not shown in FIG. 6) of wire 50 perforates the wall of receiving blood vessel 50 at the desired anastomosis site. As wire 50 is advanced within and along receiving blood vessel 50, anvil 40 and stopping element 46 are also advanced until anvil 40 becomes in contact engagement with the intima of receiving blood vessel 5 at the chosen anastomosis site. This contact engagement is preferably achieved by pulling wire 50 as indicated by arrow A in FIG. 6.

In the example shown in FIG. 6, graft vessel 9 is mounted within and around opening 30 in plate 18. Graft vessel 9 is held in position with the aid of spikes 17 that have been caused to puncture anastomosis end 7 so that such end is everted. A cutter 60 is introduced within and generally concentrically along graft vessel 9. This cutting element is embodied in some embodiments of this invention by a generally cylindrical cutter with cutting edge 62. In other embodiments of this invention, this cutting element is embodied by a surgical laser or by some other appropriate source of radiation.

A compression plate device according to this invention, such as compression plate device 10 shown in FIG. 6, is located outside receiving blood vessel 5 by inserting wire 50 within and along the openings 32 and 30 of compression plates 14 and 18, respectively. This operation permits the placement of the compression plate device 10 as shown in FIG. 6 with wire 50 running approximately from about the center of opening 32 in compression plate 14 to the center of the opening in compression plate 18 and then run within and along cutter 60.

In one embodiment of this invention, anvil 40 is a generally spherical body slidably mounted on wire 50 along one of the spherical body's diameters. In other embodiments, the anvil can be embodied by an element with a curved surface that is to be in contact engagement with the intima of the receiving blood vessel 5 at the anastomosis site. In other embodiments, the anvil is attached to wire 50, so that stopping element 46 merely provides additional support, or is simply not present.

As shown in FIG. 6, pulling wire 50 as indicated by arrow A causes anvil 40 to abut against the intima of blood vessel 5. This pulling action is exerted until the wall of blood vessel 5 is preferably distended to an extent such that the maximum cross section of anvil 40 parallel to the compression plates is past and to the right of the tips of spikes 15. A relative configuration of anvil 40 and spikes 15 satisfying this condition is illustrated in FIG. 6.

A portion of receiving blood vessel 5 is subsequently cut to open an anastomosis fenestra. Compression plate 18 is then moved towards compression plate 14 so that everted end 7 of graft vessel 9 is held closer to anvil 40, as indicated in FIG. 7. As indicated above, opening the anastomosis fenestra can be achieved by following any one among several procedures.

In one procedure, wire 50 is held so that anvil 40 cannot move backwards towards plate 14 and cutter 60 is pushed as indicated by arrow B against the anvil so that the wall of receiving blood vessel 5 is cut and cut portion 6 is held around wire 50. The tension on wire 50 is subsequently relaxed as cutter 60 is still pushed as indicated by arrow B so that spikes 15 engage the wall of blood vessel 5 as shown in FIG. 7. According to another procedure, cutter 60 is held at a fixed position with cutting edge 62 near the abutted portion of the wall of receiving blood vessel 5 and then wire 50 is pulled as indicated by arrow A in FIG. 6 against cutting edge 62 which cuts portion 6. Wire 50 is subsequently relaxed as cutter 60 is pushed as indicated by arrow B in FIG. 7 so that spikes 15 engage receiving blood vessel 5 as shown in FIG. 7. As indicated above, a cutting action can also be achieved by effectively combining the two procedures previously described, and by modifications thereof that lead to the opening of the anastomosed fenestra and to the engagement of its contour with spikes 15. Any one of these procedures will lead to the opening of an anastomosis fenestra at the anastomosis site, with the cut portion held by wire 50, and with the edges of the anastomosis fenestra open in receiving blood vessel 5 engaged with spikes 15 as shown in FIG. 7.

Compression plates 14 and 18 are subsequently brought in closer relative proximity. In one embodiment of this invention, this can be accomplished by sliding plate 18 along guides 20 as shown in FIGS. 7–8. Approximation of the compression plates causes the tips of spikes 17 to slide on the curved surface of anvil 40 and thus evert contour 8 of the anastomosis fenestra in receiving blood vessel 5 as shown in FIG. 8. The region comprising the contact engagement areas of everted edges 7 and 8 and the crossings in mating engagement of spikes 15 and 17 shown in FIG. 8 generally correspond to the region at or near line 48 shown in FIGS. 5A–5D.

Figure 9:
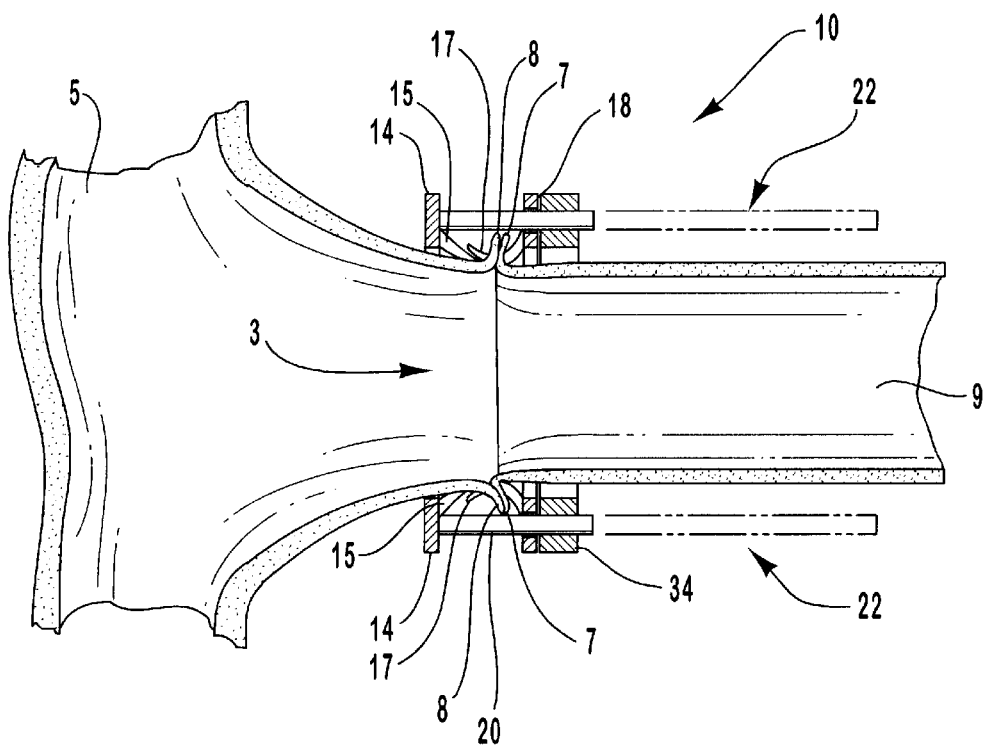
FIG. 9 shows two structures anastomosed with an embodiment of a compression plate device of this invention.

As shown in FIG. 8, everted edges 7 and 8 are in intima-intima contact and no cut portion is significantly exposed to the blood flow that is to circulate through the anastomosed structures 5 and 9. This leak-proof contact engagement of anastomosed structures 5 and 9 is schematically shown in FIGS. 8–9.

Pulling cutter 60 and wire 50 as indicated by arrow A, leads to the extraction and removal from the anastomosis site of anvil 40 with stopping element 46, wire 50 with cut portion 6, and cutter 60. Once these elements are extracted and removed, receiving blood vessel 5 and graft vessel 9 are in fluid communication through anastomosis fenestra 3, as shown in FIG. 9.

Compression plates 14 and 18 are positioned in such relative close proximity that they keep everted edges 7 and 8 in contact engagement with each other despite the circulating blood flow through anastomosis fenestra 3. In one embodiment of this invention, these edges are held in the appropriate position by spikes 15 and 17. Phantom lines in FIG. 9 show the position of terminal ends 22 after they have dissolved, clipped or otherwise removed from guides 20 in plate compression system 10.

An embodiment of a holding element, such as holding ring 34 shown in FIGS. 6–9, is part of some of the embodiments of this invention as described above. In the embodiment shown in FIG. 9 holding ring 34 keeps compression plate 18 at a substantially constant separation from compression plate 14 and prevents any significant sliding of compression plate 18 that could otherwise be caused by the pressure exerted by the circulating blood through the anastomosed structures. Holding ring 34 is moved together with compression plate 18 as indicated above regarding the sliding of compression plate 18 along guides 20.

FIG. 9 shows compression plates 14 and 18 holding the anastomosed structures by contact engagement and by penetration. Holding by contact engagement is achieved in this embodiment by the pressure exerted by compression plates 14 and 18 with the aid of holding ring 34. Holding by penetration is achieved in this embodiment by spikes 15 and 17.

It follows from the illustrations shown in FIGS. 5–9 and the foregoing discussion that the compression plates of this invention can effectively be used for anastomoses at the end of tubular structures. This implementation of the teachings described above to end-to-end anastomosis simply requires ordinary skills in the art.

Embodiments of the wire of this invention are preferably stainless steel single-use wires. Embodiments of the anvil of this invention are preferably stainless steel, abrasion resistant anvils when the cutting element is embodied by a cutter such as cutter 60. When the anastomosis fenestra is opened with a laser, the anvil of this invention is preferably coated with an appropriate radiation absorbing material. An embodiment of the anvil of this invention to be used in conjunction with embodiments of compression plates which are provided with spikes, comprises at least the portion of its surface that is to be in contact with the tips of the spikes made of an appropriate material that can withstand the scratching action of such tips.

A mechanical embodiment of a cutting element, such as cutter 60, and mechanical equivalents thereof are preferred embodiments of cutting elements because of the ease with which cut portion 6 of receiving blood vessel is retrieved and because of their relative inexpensive cost. These embodiments are preferable single use, stainless steel cutters. However, the cutting element in other embodiments of this invention is a radiation source, such as a surgical laser, that emit radiation of the appropriate characteristics to open the anastomosis fenestra in the receiving blood vessel wall. Any one of these radiation sources is typically implemented with a conventional endoscopic mechanism for its use in the practice of anastomosis.

The compression plate device of this invention is preferably embodied by a hard biocompatible material such as stainless steel, and more preferably titanium. Embodiments of synthetic graft vessels that have been successfully used in the practice of end-to-side anastomoses according to this invention include ePTFE tubular grafts.

Other embodiments of this invention supplement the effects of the compression plate anastomosis device with laser welding to enhance the leak proof character of the anastomosis. Conventional laser welding devices, including endoscopic laser welding devices, are used for this purpose.

This supplemental sealing effect is achieved in other embodiments of this invention with the appropriate use of biocompatible adhesives. These adhesives are administered by conventional delivery devices, including endoscopic glue delivery devices.

Still other embodiments of this invention rely on the sealing effects that are provided by techniques such as laser soldering, including chromophore-enhanced laser soldering, and laser sealing.

When any one of the sealing techniques is used in embodiments of this invention in conjunction with embodiments of the compression plates, the anastomosed structures are then further held by binding.

End-to-end anastomoses performed with embodiments of compression plates and anvils according to this invention comprised the anastomosis in the laboratory of ePTFE tubular grafts to receiving blood vessels, including veins and arteries. Anastomosis experiments were performed on bovine carotid arteries and external jugular veins harvested at a meat processing plant. Over 50 anastomoses were performed. The completeness of the eversion was evaluated and the anastomoses were tested for fluid-tightness. The samples were partially fixed in formalin and then the anastomosis cut in half with a high speed cutting tool. The morphology of the anastomotic junction was inspected with loupe magnification for completeness of eversion and for the presence of intraluminal metal. The anastomoses performed were fluid-tight to normal systolic pressure, and the anastomoses were morphologically satisfactory, including complete eversion of the receiving blood vessel intima with apposition to graft vessel. No intraluminal foreign material was exposed, and no subintimal connective tissue was intraluminally exposed. Creation of the anastomosis could be accomplished in as little as 60 seconds, and required no temporary occlusion of blood in the receiving blood vessel.

A non-survival in-vivo arteriovenous ePTFE graft implantation in an animal model was also successful, creating arterial and venous anastomoses with no bleeding. The chosen animal model was an adult sheep on which an ePTFE arteriovenous graft was implanted from the internal carotid artery to the external jugular vein. In the sheep the internal carotid artery is inaccessible to percutaneous puncture. This required a cutdown and significant dissection to exteriorize the internal carotid artery to a subcutaneous location, and the anastomoses were subsequently performed with good vessel eversion and no bleeding.

Embodiments of anvils whose diameters ranged from about 4 mm to about 6 mm were used in this experiments. The outer diameter of the annular compression plates used in this experiments was about 9 mm. The spikes in each embodiment of the compression plates used in these experiments were bent so that their tips were located in an imaginary circumferential contour, whose diameter ranged from about 3.5 mm to about 5.5 mm. Teeth lengths in this experiments ranged from about 1.5 mm to about 0.75 mm.

Endoscopic Implementation and Other Applicators

The positioning of the compression plate device and the operations of pulling wire 50, pushing cutter 60, and sliding compression plate 18 and holding ring 34 as described in the foregoing discussion of FIGS. 6–9 can be accomplished by manually actuating these elements or with the aid of devices such as applicators and endoscopes. One advantage derived form the use of such devices is that they comprise a series of actuators, and by manipulating these actuators the operator can effectuate the different operations at the intervention site without actually having to manually and directly operate each element itself.

One example of such devices comprises a generally coaxially mounted series of two screw-driven expanders with at least one independent arrester each. These expanders are axially perforated to allow for the passage therethrough of a wire such as wire 50. The expanders that independently act on the cutting element, such as cutter 60, and on the compression plate, such as compression plate 18, are threadably coupled and provided with a system of arresters. Because of this threaded coupling, these two expanders permit the cutting element and the simultaneous action on the compression plate and on the cutting element or the action on one of these two elements independently from the other. The expander that independently acts on a wire, such as wire 50, thus permitting to control the position of an anvil, such as anvil 40, is also provided with arresters to engage the wire. Because this expander is independent from the threadably coupled expanders that act on the compression plate and on the cutting element, the wire and the anvil can independently be acted on.

Figure 10:
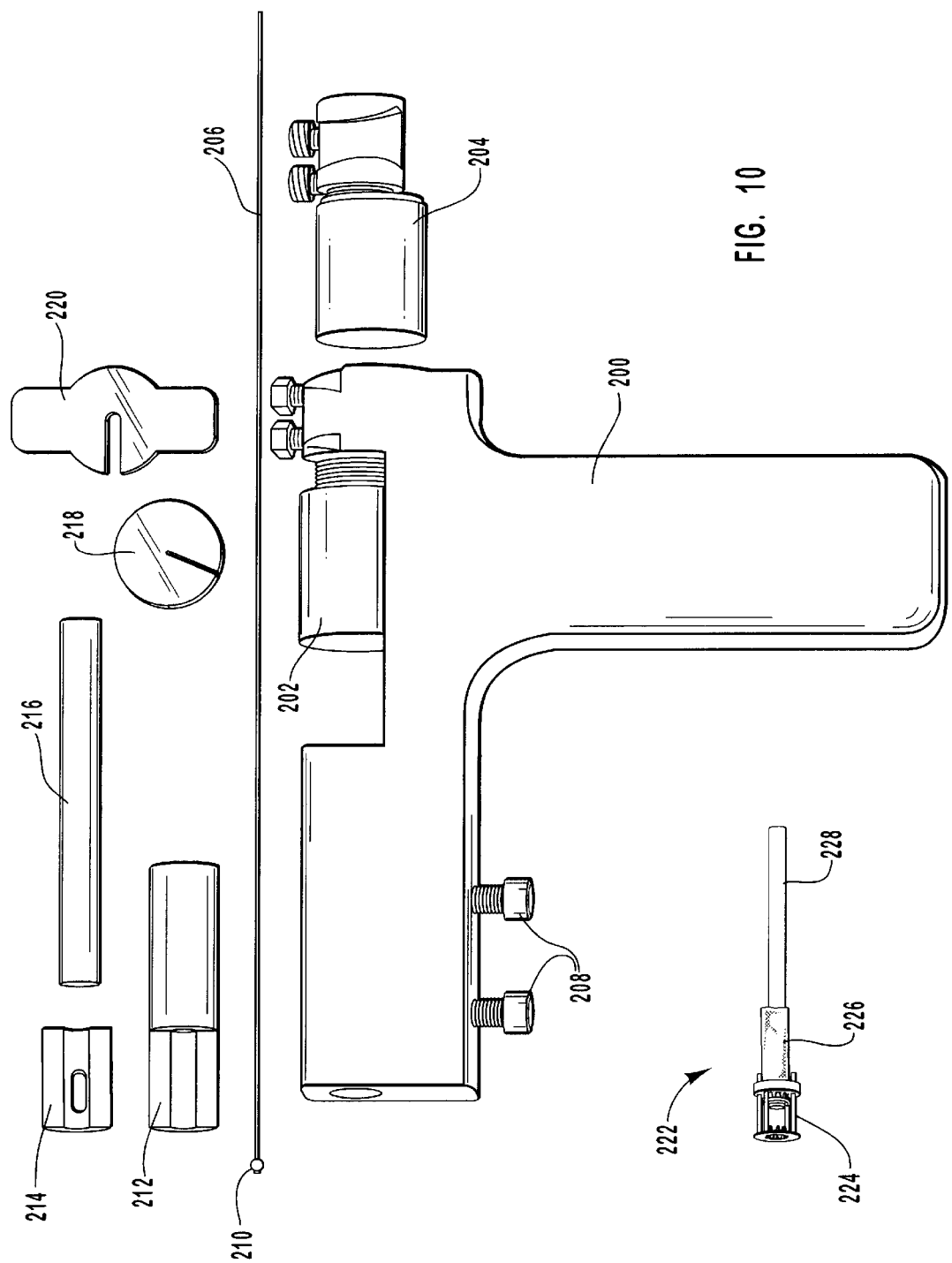
FIG. 10 shows a disassembled hand-held applicator.

In an embodiment of an applicator, these expanders, or other devices that perform equivalent functions, are either directly in contact with the elements, such as anastomosis plates and cutting element, that they control, or they actuate on these elements with the aid of simple connectors. FIG. 10 shows an embodiment of such applicator in the form of a disassembled hand-held applicator.

For assembly, an embodiment of the compression plate device 224, a graft vessel 226 and a cutter 228 are configured to form set 222. This is achieved by engaging the anastomosis end of graft vessel 226 with the graft side compression plate as shown in any of FIGS. 6–9, and by inserting cutter 228 as shown in FIG. 6. Set 222 is subsequently fitted into the applicator cylinder which is shown in FIG. 10 as mating elements 212 and 214.

This combined assembly of set 222 and applicator cylinder 212–214 is then mounted in the barrel of applicator handle 200, and fixed into place with setscrews 208. Cutter advancing shim 218 is mounted in the breach between distal expander 202 and the end of the cutter opposite to the cutter's cutting edge. Graft side compression plate advancing shim 220 is mounted immediately in front of the cutter advancing shim 218 with its larger slot over the back of cutter 228, and in position to advance graft side compression plate push rod 216.

The embodiment of the applicator of this invention shown in FIG. 10 is used in the practice of anastomosis according to procedures such as the procedure described hereinbelow as an example. Under direct image guidance, a sheath is advanced from a distant percutaneous puncture to the anastomosis site based upon a diagnostic angiographic roadmap. A skin incision and limited vessel dissection is performed at the anastomosis site to expose the vessel wall. Anvil 210 and wire 206 are inserted into the sheath and the wire tip advanced through the receiving vessel wall. In this embodiment of the invention, anvil 210 is integrally attached to the end of wire 206 opposite to this wire's piercing end. The wire tip is grasped externally and pulled through the puncture until the anvil is tight against the intima of the receiving vessel.

The assembled applicator is approached to the intervention region, the curved tip of the wire is removed with diagonal cutters, and the wire is advanced into the preassembled applicator until the receiving vessel wall is in contact with the receiving vessel side compression plate. Set screws on distal expander 202 are temporarily tightened and proximal expander 204 is placed over wire 206 and tightened in place. The distal expander 202 screws are subsequently loosened and proximal expander 204 is expanded by applying force to bring the anvil and the receiving vessel wall through the opening of the receiving vessel side compression plate. Distal expander 202 is then expanded causing cutter 228 to be driven against the curved, preferably spherical, anvil surface, thus opening a circular anastomosis fenestra.

Finally, manual force on the graft side compression vessel advancing shim 220 drives graft side compression plate push rod 216 and the graft side compression plate towards the receiving vessel side compression plate. The graft side compression plate spikes engage the receiving vessel at sites near the contour of the anastomosis fenestra and, as they are forced over the surface of anvil 210, the contour of the anastomosis fenestra is everted and trapped between the two compression plate spikes.

In the embodiment of the compression plate device 224, the guides are welded to the anastomosis side of the receiving vessel side compression plate. The graft side compression plate slides over the guides, with the holding ring providing a friction couple to maintain position after the compression plates have been correctly positioned relative to each other. The excess lengths of the guides are clipped off with diagonal cutters. The applicator cylinder is slid out of the handle and disassembled. Anvil 210 and wire 206 are pulled out through the graft vessel with the cut portion of the receiving blood vessel.

In other embodiments, these expanders, or other devices that perform equivalent functions, are mounted at the proximal end of an endoscope which in addition can be provided with a plurality of ports and conduits. These additional ports and conduits permit the access of the anastomosis site by other devices such as aspirators, rinsers, imaging devices, probes, and in general devices that are known to be part of endoscopic interventional and exploratory apparatuses. Whether the mounting for the expanders or other equivalent devices is endoscopic or otherwise, such mounting provides in some embodiments guides, rails, channels or equivalent structures to facilitate the relative orientation of the compression plates of this invention and their positioning at the anastomosis sites. These guides, rails, channels and equivalent structures thereof are additional examples of embodiments of means for guiding the movement of one compression plate with respect to the other compression plate. In addition, these guides, rails, channels and equivalent structures thereof are examples of means for moving the compression plate device.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A compression plate anastomosis device for anastomosing structures, comprising:

a first compression plate having an anastomosis side, the first compression plate having an opening;

a second compression plate having an anastomosis side, said second compression plate having an opening;

first holding means for holding a first vessel, wherein the first holding means is attached to said first compression plate;

second holding means for holding a second vessel, wherein the second holding means is attached to said second compression plate;

means for guiding the movement of said second compression plate relative to said first compression plate, wherein the guiding means extend perpendicularly from the first compression plate and are positioned relative to the first holding means in a manner that enables the first vessel to be everted on the first holding means, wherein said second compression plate is movably positioned on the guiding means such that said second compression plate is in a parallel orientation relative to said first compression plate, wherein the guiding means have a length and configuration that permits the first and second vessels to be initially spaced apart and opposite from each other as said second compression plate is movably positioned on the guiding means with said second vessel being held on the second holding means and while the first vessel is held by the first holding means of the first compression plate until the second compression plate is moved on the guiding means toward the first compression plate to bring the second vessel into contact with the first vessel for anastomosis.

2. A compression plate anastosis device as recited in claim 1, wherein said guiding means comprises a plurality of guides and each guide has a first end attached to said anastomosis side of said first compression plate and an opposite terminal end, and wherein each guide has a length such that it is necessary to eliminate each terminal end after the anastomosis.

3. A compression plate anastomosis device as recited in claim 1, wherein each holding means comprises a plurality of spikes extending from said anastomosis side of each compression plate.

4. A compression plate anastomosis device as recited in claim 1, wherein said first and second holding means respectively extend nonperpendicularly and radially inward from the anastomosis side of each respective first and second compression plate.

5. A compression plate anastomosis device as recited in claim 1, wherein said first and second holding means respectively extend perpendicularly from the anastomosis side of each respective first and second compression plate.

6. A compression plate anastomosis device as recited in claim 1, wherein said first holding means are in mating configuration with respect to said second holding means once the second vessel is brought into contact with the first vessel for anastomosis.

7. A compression plate anastomosis device as recited in claim 1, wherein said first and second holding means are configured for respectively holding the first and second vessels through penetrating the first and second vessels.

8. A compression plate anastomosis device as recited in claim 1, wherein said first and second holding means have flat tips and are configured respectively for holding the first and second vessels through contact engagement without penetration.

9. A compression plate anastomosis device as recited in claim 1, wherein each first and second holding means has a base and terminates at a pointed puncturing tip.

10. A compression plate anastomosis device as recited in claim 1, wherein each first and second holding means has a base and terminates at a flat tip.

11. A compression plate anastomosis device as recited in claim 1, wherein each first and second holding means is flexible.

12. A compression plate anastomosis device as recited in claim 1, wherein said first and second compression plates each have an outer periphery and each have an inner periphery at their respective opening, wherein said first and second holding means are located between the outer and inner peripheries on the anastomosis sides of the respective first and second compression plates.

13. A compression plate anastomosis device as recited in claim 1, wherein said first and second compression plates each have an inner periphery at their respective opening, wherein said first and second holding means are located on the inner peripheries of the respective first and second compression plates.

14. A compression plate anastomosis device as recited in claim 1, further comprising a holding ring positioned on the second compression plate opposite from the anastomosis side, wherein the holding ring is movable on the guiding means with the second compression plate while providing sufficient frictional resistance to keep the second compression plate at a desired location on the guiding means.

15. A compression plate anastomosis device for anastomosing structures, comprising:
 a first compression plate having an anastomosis side, the first compression plate having an opening;
 a second compression plate having an anastomosis side, said second compression plate having an opening;
 a first plurality of spikes extending from said first compression plate to engage a first vessel;
 a second plurality of spikes extending from said second compression plate to engage a second vessel;
 a plurality of guides extending from the first compression plate, wherein the second compression plate is movably positioned on the guides, wherein the guides are positioned relative to the first and second plurality of spies and have a length that permits the first and second vessels to be initial spaced apart and opposite from each other as said second compression plate is movably positioned on the guides with said second vessel being held on the second plurality of spikes and while the first vessel is held by the first plurality of spikes of the first compression plate until the second compression plate is moved on the guides toward the first compression plate to bring the second vessel into contact with the first vessel for anastomosis.

16. A compression plate anastomosis device as recited in claim 15, wherein each guide has a first end extending from said anastomosis side of said first compression plate and an opposite terminal end, and wherein each guide has a length such that it is necessary to eliminate each terminal end after the anastomosis.

17. A compression plate anastomosis device as recited in claim 15, wherein said first and second plurality of spikes respectively extend nonperpendicularly and radially inward from the anastomosis side of each respective first and second compression plate.

18. A compression plate anastomosis device as recited in claim 15, wherein said first and second plurality of spikes respectively extend perpendicularly from the anastomosis side of each respective first and second compression plate.

19. A compression plate anastomosis device as recited in claim 15, wherein said first plurality of spikes are in mating configuration with respect to said second plurality of spikes once the second vessel is brought into contact with the first vessel for anastomosis.

20. A compression plate anastomosis device as recited in claim 15, wherein said first and second plurality of spikes are configured for respectively holding the first and second vessels through penetrating the first and second vessels.

21. A compression plate anastomosis device as recited in claim 15, wherein each spike of said first and second plurality of spikes has a flat tip, and wherein the first and second plurality of spikes are configured respectively for holding the first and second vessels through contact engagement without penetration.

22. A compression plate anastomosis device as recited in claim 15, wherein each spike of said first and second plurality of spikes has a base and terminates at a pointed puncturing tip.

23. A compression plate anastomosis device as recited in claim 15, wherein each spike of said first and second plurality of spikes has a base and terminates at a flat tip.

24. A compression plate anastomosis device as recited in claim 15, wherein each spike of said first and second plurality of spikes is flexible.

25. A compression plate anastomosis device as recited in claim 15, wherein said first and second compression plates each have an outer periphery and each have an inner periphery at their respective opening, wherein said first and second plurality of spikes are located between the outer and inner peripheries on the anastomosis sides of the respective first and second compression plates.

26. A compression plate anastomosis device as recited in claim 15, wherein said first and second compression plates each have an inner periphery at their respective opening, wherein said first and second plurality of spikes are located on the inner peripheries of the respective first and second compression plates.

27. A compression plate anastomosis device as recited in claim 15, further comprising a holding ring positioned on the second compression plate opposite from the anastomosis side, wherein the holding ring is movable on the plurality of guides with the second compression plate while providing sufficient frictional resistance to keep the second compression plate at a desired location on the plurality of guides.

28. A compression plate anastomosis device for anastomosing structures, comprising:
 a first compression plate having an anastomosis side, the first compression plate having an opening;
 a second compression plate having an anastomosis side, said second compression plate having an opening;
 a first plurality of spikes extending from said first compression plate to engage a first vessel;
 a second plurality of spikes extending from said second compression plate to engage a second vessel, wherein said second plurality of spikes are positioned such that said second plurality of spikes are in mating configuration with respect to said first plurality of spikes once the second vessel is brought into contact with the first vessel for anastomosis;
 a plurality of guides extending from the first compression plate, wherein the second compression plate is movably positioned on the guides, wherein the guides are positioned relative to the first and second plurality of spikes and have a length that permits the first and second vessels to be initially spaced apart and opposite from each other as said second compression plate is movably positioned on the guides with said second vessel being held on the second plurality of spikes and while the first vessel is held by the first plurality of spikes of the first compression plate until the second compression plate is moved on the guides toward the first compression plate to bring the second vessel into contact with the first vessel for the anastomosis.

29. A compression plate anastomosis device for anastomosing structures, comprising:

a first compression plate having an anastomosis side, the first compression plate having an opening;

a second compression plate having an anastomosis side, said second compression plate having an opening;

a first plurality of spikes extending from said first compression plate to engage a first vessel;

a second plurality of spikes extending from said second compression plate to engage a second vessel;

a plurality of guides extending from the first compression plate, wherein the plurality of guides and the first plurality of spikes are positioned relative to each other in a manner that enables the first vessel to be everted on the first plurality of spikes, wherein the second compression plate is movably positioned on the guides, wherein the guides are positioned relative to the first and second plurality of spikes and have a length that permits the first and second vessels to be initially spaced apart and opposite from each other as said second compression plate is movably positioned on the guides with said second vessel being held on the second plurality of spikes and while the first vessel is held by the first plurality of spikes of the first compression plate until the second compression plate is moved on the guides toward the first compression plate to bring the second vessel into contact with the first vessel for anastomosis.

30. A compression plate anastomosis device as recited in claim 29, wherein each guide has a first end extending from said anastomosis side of said first compression plate and an opposite terminal end, and wherein each guide has a length such that it is necessary to eliminate each terminal end after the anastomosis.

31. A compression plate anastomosis device as recited in claim 29, wherein said first and second plurality of spikes respectively extend nonperpendicularly and radially inward from the anastomosis side of each respective first and second compression plate.

32. A compression plate anastomosis device as recited in claim 29, wherein said first and second plurality of spikes respectively extend perpendicularly from the anastomosis side of each respective first and second compression plate.

33. A compression plate anastomosis device as recited in claim 29, wherein said first plurality of spikes are in mating configuration with respect to said second plurality of spikes once the second vessel is brought into contact with the first vessel for anastomosis.

34. A compression plate anastomosis device as recited in claim 29, wherein said first and second plurality of spikes are configured for respectively holding the first and second vessels through penetrating the first and second vessels.

35. A compression plate anastomosis device as recited in claim 29, wherein each spike of said first and second plurality of spikes has a flat tip, and wherein the first and second plurality of spikes are configured respectively for holding the first and second vessels through contact engagement without penetration.

36. A compression plate anastomosis device as recited in claim 29, wherein each spike of said first and second plurality of spikes has a base and terminates at a pointed puncturing tip.

37. A compression plate anastomosis device as recited in claim 29, wherein each spike of said first and second plurality of spikes has a base and terminates at a flat tip.

38. A compression plate anastomosis device as recited in claim 29, wherein each spike of said first and second plurality of spikes is flexible.

39. A compression plate anastomosis device as recited in claim 29, wherein said first and second compression plates each have an outer periphery and each have an inner periphery at their respective opening, wherein said first and second plurality of spikes are located between the outer and inner peripheries on the anastomosis sides of the respective first and second compression plates.

40. A compression plate anastomosis device as recited in claim 29, wherein said first and second compression plates each have an inner periphery at their respective opening, wherein said first and second plurality of spikes are located on the inner peripheries of the respective first and second compression plates.

41. A compression plate anastomosis device as recited in claim 29, further comprising a holding ring positioned on the second compression plate opposite from the anastomosis side, wherein the holding ring is movable on the plurality of guides with the second compression plate while providing sufficient frictional resistance to keep the second compression plate at a desired location on the plurality of guides.

42. A compression plate anastomosis device for anastomosing structures, comprising:

a first compression plate having an anastomosis side, the first compression plate having an opening;

a second compression plate having an anastomosis side, said second compression plate having an opening;

a first plurality of spikes extending from said first compression plate to engage a first vessel, wherein each spike terminates at a tip;

a second plurality of spikes extending from said second compression plate to engage a second vessel;

a plurality of guides extending from the first compression plate, wherein the guides are disposed radially further from the center of the opening in the first compression plate than the tip of each spike in the first plurality of spikes, wherein the second compression plate is movably positioned on the guides, wherein the guides are positioned relative to the first and second plurality of spikes and have a length that permits the first and second vessels to be initially spaced apart and opposite from each other as said second compression plate is movably positioned on the guides with said second vessel being held on the second plurality of spikes and while the first vessel is held by the first plurality of spikes of the first compression plate until the second compression plate is moved on the guides toward the first compression plate to bring the second vessel into contact with the first vessel for anastomosis.

* * * * *

UNITED STATES PATENT AND TRADEMARK OFFICE
CERTIFICATE OF CORRECTION

PATENT NO. : 6,569,173 B1
APPLICATION NO. : 09/460740
DATED : May 27, 2003
INVENTOR(S) : Duane D. Blatter et al.

It is certified that error appears in the above-identified patent and that said Letters Patent is hereby corrected as shown below:

Column 10, line 46: Joseph "Losealzo" should be Joseph --Loscalzo.--

Column 23, line 22: the sentence should read, --For example, any one of these cutting actions. . .-- rather than ". . .any one of this cutting actions. . ."

Column 24, line 1: the word "application" should be plural, --applications,-- as there are two applications being referenced.

Column 26, line 59: the word "chamfered" should be --chambered.--

Column 31, line 55 and 57: the word "this" should be --these.--

Column 35, line 37 Claim 15: the word "spies" should be --spikes.--

Signed and Sealed this

Fifteenth Day of April, 2008

JON W. DUDAS
*Director of the United States Patent and Trademark Office*